(12) United States Patent
Qian et al.

(10) Patent No.: US 11,384,065 B2
(45) Date of Patent: Jul. 12, 2022

(54) HETEROCYCLIC COMPOUND AS CSF-1R INHIBITOR AND USE THEREOF

(71) Applicant: MEDSHINE DISCOVERY INC., Jiangsu (CN)

(72) Inventors: Wenyuan Qian, Shanghai (CN); Chundao Yang, Shanghai (CN); Guanghai Xu, Shanghai (CN); Jie Li, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 14 days.

(21) Appl. No.: 16/959,706

(22) PCT Filed: Jan. 3, 2019

(86) PCT No.: PCT/CN2019/070228
§ 371 (c)(1),
(2) Date: Jul. 2, 2020

(87) PCT Pub. No.: WO2019/134662
PCT Pub. Date: Jul. 11, 2019

(65) Prior Publication Data
US 2021/0107894 A1    Apr. 15, 2021

(30) Foreign Application Priority Data
Jan. 3, 2018 (CN) .......................... 201810005326.1

(51) Int. Cl.
*C07D 401/14* (2006.01)
*A61K 9/00* (2006.01)

(52) U.S. Cl.
CPC .......... *C07D 401/14* (2013.01); *A61K 9/0019* (2013.01); *A61K 9/0053* (2013.01)

(58) Field of Classification Search
CPC .................................................. C07D 401/14
See application file for complete search history.

(56) References Cited

U.S. PATENT DOCUMENTS

| 2005/0026976 A1 | 2/2005 | Curtin et al. |
| 2010/0076051 A1 | 3/2010 | Curtin et al. |
| 2011/0275630 A1 | 11/2011 | Matulenko et al. |

FOREIGN PATENT DOCUMENTS

| WO | 2004108672 A1 | 12/2004 |
| WO | 2012047017 A2 | 4/2012 |
| WO | WO-2013052394 A1 | 4/2013 |
| WO | WO-2014001802 A1 | 1/2014 |
| WO | WO-2017068412 A1 | 4/2017 |
| WO | WO-2019134661 A1 | 7/2019 |

OTHER PUBLICATIONS

Extended European Search Report regarding EP 19736182.7, dated May 31, 2021.

*Primary Examiner* — Brian E McDowell
(74) *Attorney, Agent, or Firm* — Harness, Dickey & Pierce, P.L.C.

(57) ABSTRACT

The present invention relates to a class of isoindolinone derivatives and use thereof in the preparation of a medicament for treating diseases associated with a novel colony stimulating factor 1 receptor (CSF-1R) inhibitor. In particular, the present invention relates to a compound of formula (I) and a pharmaceutically acceptable salt thereof or a stereoisomer thereof.

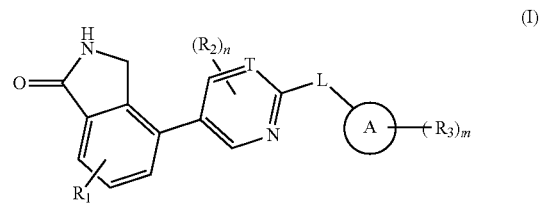

19 Claims, No Drawings

HETEROCYCLIC COMPOUND AS CSF-1R INHIBITOR AND USE THEREOF

CROSS-REFERENCE TO RELATED APPLICATIONS

This application is a 371 National Phase of International Application No. PCT/CN2019/070228, filed Jan. 3, 2019, which claims the benefit of Chinese Patent Application No. CN 201810005326.1, filed Jan. 3, 2018. The entire disclosures of the above applications are incorporated herein by reference.

TECHNICAL FIELD

The present invention relates to a class of isoindolinone derivatives and use thereof in the preparation of a medicament for treating diseases associated with a novel colony stimulating factor 1 receptor (CSF-1R) inhibitor. In particular, the present invention relates to a compound of formula (I) and a pharmaceutically acceptable salt thereof or a stereoisomer thereof.

BACKGROUND ART

Colony stimulating factor 1 (CSF-1, also known as macrophage colony stimulating factor, M-CSF) is an important growth factor that controls the growth of bone marrow progenitor cells, monocytes, macrophages, and osteoclasts and dendritic cells differentiated from macrophages, and must bind to its only cell surface receptor CSF-1R to exert its biological effects. CSF-1R is encoded by proto-oncogene c-FMS, so it is also called c-FMS, and is a receptor tyrosine kinase. The binding of CSF-1 with CSF-1R in the extracellular domain induces the dimerization of CSF-1R, which further leads to autophosphorylation of the CSF-1R kinase region in the cell. Once phosphorylation occurs, CSF-1R acts as a docking site for several cytoplasmic signaling molecules, eventually triggering a series of signaling cascades. For example, the phosphorylation on the tyrosine residue 697 of CSF-1R can activate the MAPK signaling pathway, while the phosphorylation on its tyrosine residue 721 can initiate the PI3K and PLCγ signaling pathways.

Many tumor cells can secrete growth factors like CSF-1 during the growth process, and the latter can recruit macrophages (tumor-associated macrophage, TAM) to enter the tumor area. Macrophages can secrete CSF-1 just like tumor cells, and their entrance promotes the formation of a complex microenvironment for tumors, which can help tumor cells to develop immune tolerance to autoimmune function, thereby promoting the proliferation, invasion and metastasis of tumor cells in the body. Through the inhibition of CSF-1R, it may be beneficial to treat diseases caused by lesions of osteoclasts, dendritic cells and macrophages, such as autoimmune/infectious diseases, cancers, and bone-related diseases.

Recent studies have shown that inhibitors of CSF-1R can be used in the field of disease treatment in various ways. It can be used alone or in combination with various anti-cancer therapies, such as anti-angiogenesis, adoptive transfer of T cells, radiotherapy, chemotherapy, and immune checkpoint therapy. Many marketed drugs have inhibitory activity on CSF-1R, such as imatinib, dasatinib, and sunitinib, but selective CSF-1R inhibitors have not yet been marketed. Pexidartinib (PLX-3397), developed by Plexxikon and acquired by Daiichi Sankyo, is a dual inhibitor of CSF-1R and c-Kit. It is currently in clinical phase three, and is used to treat a variety of cancers such as giant cell tumor of tendon sheath (TGCT). Array's ARRY-382 and Novartis' BLZ-945 are more selective CSF-1R inhibitors, and are currently in clinical phase two.

Patent US2005026976 discloses a control compound, and the main target of the control compound is KDR, and the control compound is used to treat tumors and cancers, and has a structure as follows.

Control Compound

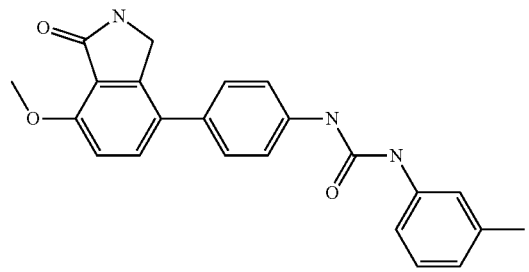

SUMMARY OF THE INVENTION

The present invention provides a compound represented by formula (I) and a pharmaceutically acceptable salt thereof or a stereoisomer thereof:

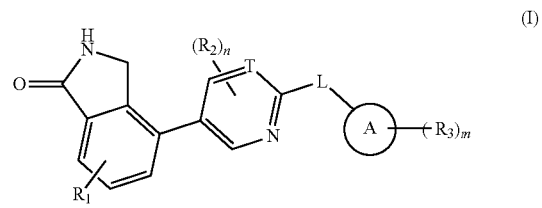

wherein

T is selected from —N— and —CH—;

$R_1$ is selected from $N(R_4)(R_5)$;

$R_2$ is independently selected from H, F, Cl, Br, I, OH, $NH_2$ and CN, or is independently selected from $C_{1-3}$ alkyl optionally substituted with 1, 2 or 3R;

$R_3$ is independently selected from H, F, Cl, Br, I, OH, $NH_2$, CN, $C_{1-6}$ alkyl, $C_{1-6}$ heteroalkyl, $C_{3-7}$ cycloalkyl and $C_{3-7}$ cycloalkyl-O—, and the $C_{1-6}$ alkyl, $C_{1-6}$ heteroalkyl, $C_{3-7}$ cycloalkyl and $C_{3-7}$ cycloalkyl-O— are optionally substituted with 1, 2 or 3R;

$R_4$ and $R_5$ are each independently selected from H, $C_{1-3}$ alkyl and $C_{1-3}$ alkyl-C(=O)—, and the $C_{1-3}$ alkyl and $C_{1-3}$ alkyl-C(=O)— are optionally substituted with 1, 2 or 3 substituents independently selected from F, Cl, Br, I, $NH_2$ and OH;

L is selected from —NH— and —NHCH$_2$—;

Ring A is selected from phenyl, 5-6 membered heteroaryl and 6 membered heterocycloalkenyl;

n is selected from 0, 1 and 2;

m is selected from 1, 2 and 3;

Each R is independently selected from H, F, Cl, Br, I, OH, $NH_2$, CN, $C_{1-6}$ alkyl and $C_{1-6}$ heteroalkyl, and the $C_{1-6}$ alkyl and $C_{1-6}$ heteroalkyl are optionally substituted with 1, 2 or 3R';

R' is selected from F, Cl, Br, I, OH, $NH_2$, CN and Me;

The $C_{1-6}$ heteroalkyl, 5-6 membered heteroaryl and 6 membered heterocycloalkenyl independently contain 1, 2, 3 or 4 heteroatoms or heteroatomic groups independently selected from —O—, —S—, N or —NH—.

In some embodiments of the present invention, the above R is selected from H, F, Cl, Br, I, OH, $NH_2$, CN, $C_{1-3}$ alkyl and $C_{1-3}$ alkoxy, and the $C_{1-3}$ alkyl and $C_{1-3}$ heteroalkyl are optionally substituted with 1, 2 or 3R', and other variables are as defined in the present invention.

In some embodiments of the present invention, the above R is selected from H, F, Cl, Br, I, OH, $NH_2$, CN, Me, Et,

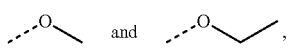

and the Me, Et,

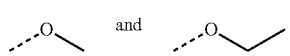

are optionally substituted with 1, 2 or 3R', and other variables are as defined in the present invention.

In some embodiments of the present invention, the above R is selected from H, F, Cl, Br, I, OH, $NH_2$, CN, Me, $CH_2F$, $CHF_2$, $CF_3$, Et,

and other variables are as defined in the present invention.

In some embodiments of the present invention, the above $R_2$ is independently selected from H, F, Cl, Br, I, OH, $NH_2$, CN, Me and Et, and the Me and Et are optionally substituted with 1, 2 or 3R, and other variables are as defined in the present invention.

In some embodiments of the present invention, the above $R_2$ is selected from Me, and other variables are as defined in the present invention.

In some embodiments of the present invention, the above $R_3$ is independently selected from H, F, Cl, Br, I, OH, $NH_2$, CN, $C_{1-3}$ alkyl, $C_{1-3}$ alkoxy, $C_{1-3}$ alkylamino, cyclopropanyl and cyclopropanyl-O—, and the $C_{1-3}$ alkyl, $C_{1-3}$ alkoxy, $C_{1-3}$ alkylamino, cyclopropanyl and cyclopropanyl-O— are optionally substituted with 1, 2 or 3R, and other variables are as defined in the present invention.

In some embodiments of the present invention, the above 121 is independently selected from H, F, Cl, Br, I, OH, $NH_2$, CN, Me,

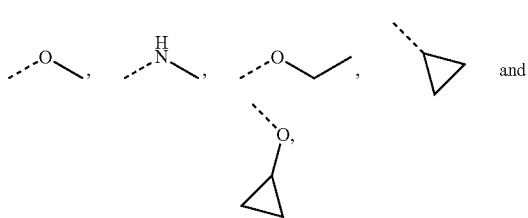

and the Me,

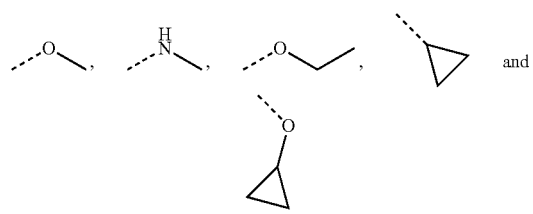

are optionally substituted with 1, 2, or 3R, and other variables are as defined in the present invention.

In some embodiments of the present invention, the above $R_3$ is selected from H, F, Cl, Br, I, OH, $NH_2$, CN, Me,

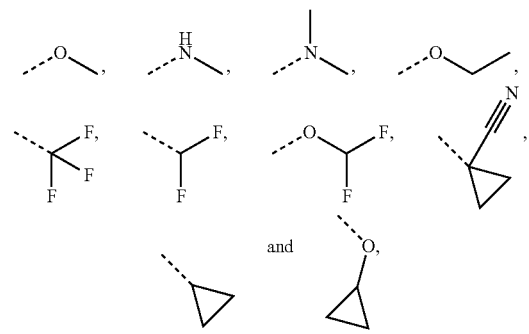

and other variables are as defined in the present invention.

In some embodiments of the present invention, the above $R_4$ and $R_5$ are independently selected from H, Me, Et and

and other variables are as defined in the present invention.

In some embodiments of the present invention, the above $R_1$ is selected from $NH_2$,

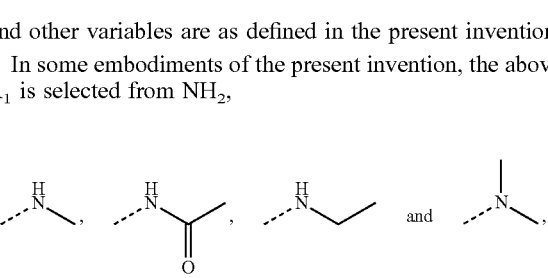

and other variables are as defined in the present invention.

In some embodiments of the present invention, the above ring A is selected from phenyl, pyridazinyl, pyrazinyl, pyrimidinyl, pyridin-2(1H)one and pyridyl, and other variables are as defined in the present invention.

In some embodiments of the present invention, the above structural unit

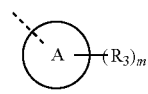

is selected from
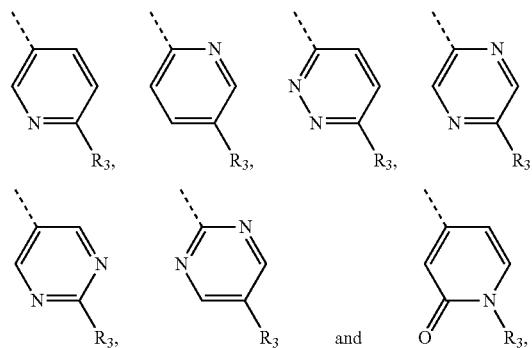
and other variables are as defined in the present invention.
In some embodiments of the present invention, the above structural unit
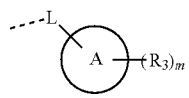
is selected from
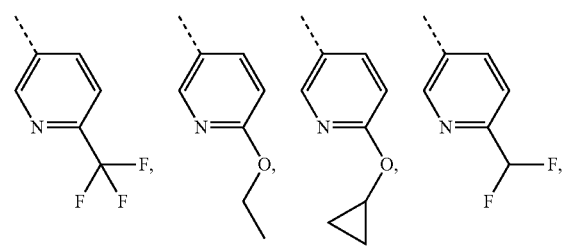
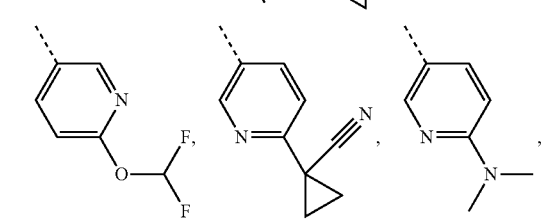
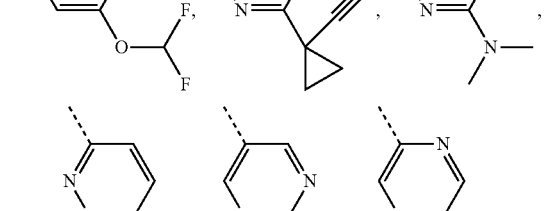
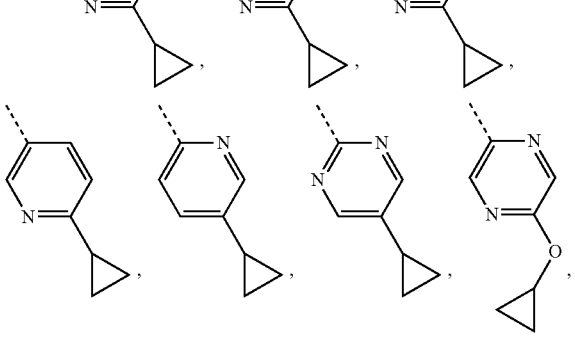
-continued
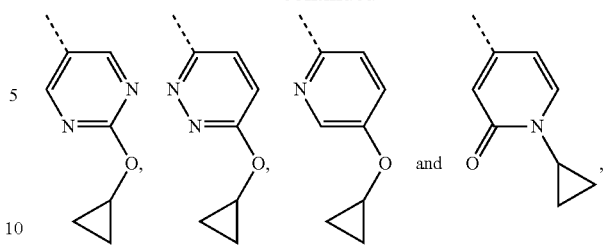
and other variables are as defined in the present invention.
In some embodiments of the present invention, the above structural unit
is selected from
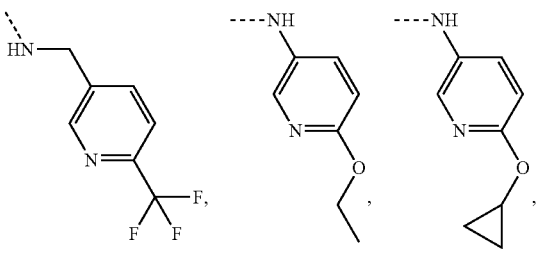
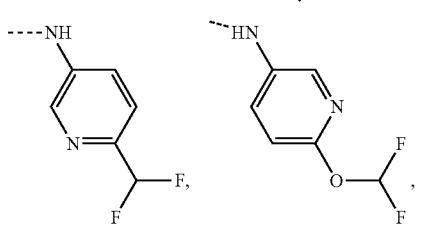
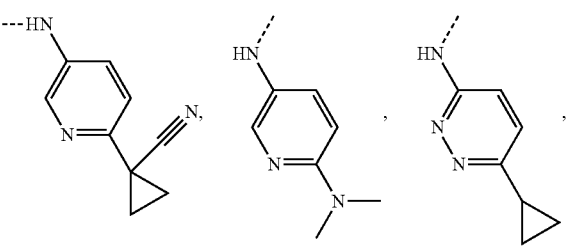
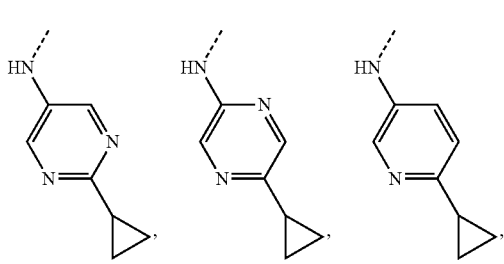

-continued

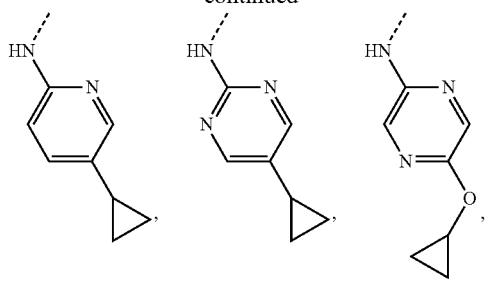

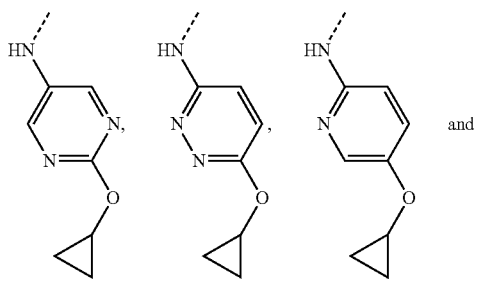

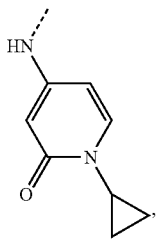

and other variables are as defined in the present invention.

In some embodiments of the present invention, the above structural unit

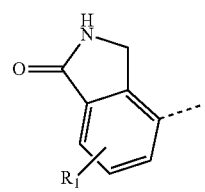

is selected from

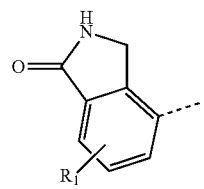

is selected from

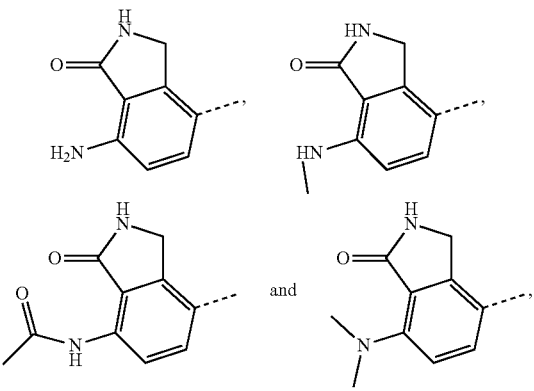

and other variables are as defined in the present invention.

In some embodiments of the present invention, the above structural unit

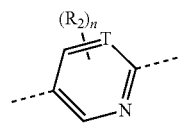

is selected from

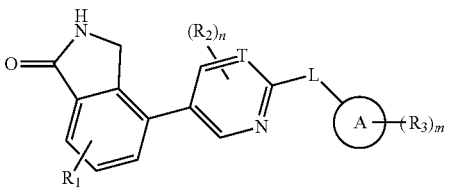

and other variables are as defined in the present invention.

The present invention provides a compound represented by formula (I) and a pharmaceutically acceptable salt thereof or a stereoisomer thereof:

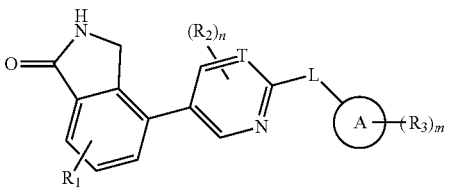

wherein

T is selected from —N— and —CH—;

$R_1$ is selected from $N(R_4)(R_5)$;

$R_2$ is independently selected from H, F, Cl, Br, I, OH, $NH_2$ and CN, or is independently selected from $C_{1-3}$ alkyl optionally substituted with 1, 2 or 3R;

$R_3$ is independently selected from H, F, Cl, Br, I, OH, $NH_2$, CN, $C_{1-6}$ alkyl, $C_{1-6}$ heteroalkyl, $C_{3-7}$ cycloalkyl and $C_{3-7}$ cycloalkyl-O—, and the $C_{1-6}$ alkyl, $C_{1-6}$ heteroalkyl, $C_{3-7}$ cycloalkyl and $C_{3-7}$ cycloalkyl-O— are optionally substituted with 1, 2 or 3R;

$R_4$ and $R_5$ are each independently selected from H, $C_{1-3}$ alkyl and $C_{1-3}$ alkyl-C(=O)—, and the $C_{1-3}$ alkyl and $C_{1-3}$ alkyl-C(=O)— are optionally substituted with 1, 2 or 3 substituents independently selected from F, Cl, Br, I, $NH_2$ and OH;

L is selected from —NH— and —$NHCH_2$—;

ring A is selected from phenyl and 5-6 membered heteroaryl;

n is selected from 0, 1 and 2;

m is selected from 1, 2 and 3;

Each R is independently selected from H, F, Cl, Br, I, OH, $NH_2$, CN, $C_{1-6}$ alkyl and $C_{1-6}$ heteroalkyl, and the $C_{1-6}$ alkyl and $C_{1-6}$ heteroalkyl are optionally substituted with 1, 2 or 3 R';

R' is selected from F, Cl, Br, I, OH, $NH_2$, CN and Me;

The $C_{1-6}$ heteroalkyl and 5-6 membered heteroaryl independently contain 1, 2, 3 or 4 heteroatoms or heteroatomic groups independently selected from —O—, —S—, N or —NH—.

In some embodiments of the present invention, the above R is selected from H, F, Cl, Br, I, OH, $NH_2$, CN, $C_{1-3}$ alkyl and $C_{1-3}$ alkoxy, and the $C_{1-3}$ alkyl and $C_{1-3}$ heteroalkyl are optionally substituted with 1, 2 or 3 R', and other variables are as defined in the present invention.

In some embodiments of the present invention, the above R is selected from H, F, Cl, Br, I, OH, $NH_2$, CN, Me, Et,

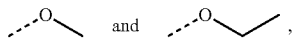

and the Me, Et,

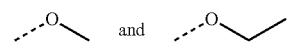

are optionally substituted with 1, 2 or 3 R', and other variables are as defined in the present invention.

In some embodiments of the present invention, the above R is selected from H, F, Cl, Br, I, OH, $NH_2$, CN, Me, $CH_2F$, $CHF_2$, $CF_3$, Et,

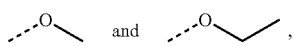

and other variables are as defined in the present invention.

In some embodiments of the present invention, the above $R_2$ is independently selected from H, F, Cl, Br, I, OH, $NH_2$, CN, Me and Et, and the Me and Et are optionally substituted with 1, 2, or 3R, and other variables are as defined in the present invention.

In some embodiments of the present invention, the above $R_2$ is selected from Me, and other variables are as defined in the present invention.

In some embodiments of the present invention, the above $R_3$ is independently selected from H, F, Cl, Br, I, OH, $NH_2$, CN, $C_{1-3}$ alkyl, $C_{1-3}$ alkoxy, cyclopropanyl and cyclopropanyl-O—, and the $C_{1-3}$ alkyl, $C_{1-3}$ alkoxy, cyclopropanyl and cyclopropanyl-O— are optionally substituted with 1, 2 or 3R, and other variables are as defined in the present invention.

In some embodiments of the present invention, the above $R_3$ is independently selected from H, F, Cl, Br, I, OH, $NH_2$, CN, Me,

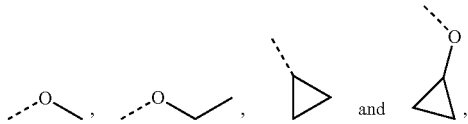

and the Me,

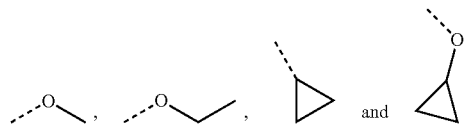

are optionally substituted with 1, 2 or 3R, and other variables are as defined in the present invention.

In some embodiments of the present invention, the above $R_3$ is independently selected from H, F, Cl, Br, I, OH, $NH_2$, CN, Me,

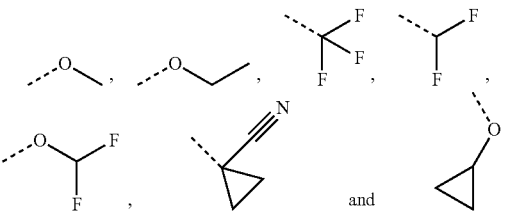

and other variables are as defined in the present invention.

In some embodiments of the present invention, the above $R_4$ and $R_5$ are independently selected from H, Me, Et and

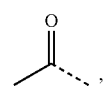

and other variables are as defined in the present invention.

In some embodiments of the present invention, the above $R_1$ is selected from $NH_2$,

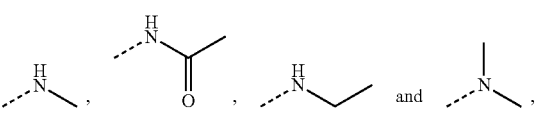

and other variables are as defined in the present invention.

In some embodiments of the present invention, the above ring A is selected from phenyl and pyridyl, and other variables are as defined in the present invention.

In some embodiments of the present invention, the above structural unit is selected from

[Structure: A ring with (R₃)ₘ substituent]

is selected from

[Pyridine structure with R₃ substituent]

and other variables are as defined in the present invention.

In some embodiments of the present invention, the above structural unit

[Structure: A ring with (R₃)ₘ substituent]

is selected from

[Five pyridine-based structures with various substituents: CF₃, OEt, O-cyclopropyl, CHF₂, OCHF₂]

and

[Pyridine with cyclopropyl-CN substituent]

and other variables are as defined in the present invention.

In some embodiments of the present invention, the above structural unit

[Structure: L—A ring with (R₃)ₘ substituent]

is selected from

[Six aminopyridine structures with substituents: HN-CH₂-pyridine-CF₃, NH-pyridine-OEt, NH-pyridine-O-cyclopropyl, NH-pyridine-CHF₂, HN-pyridine-OCHF₂, HN-pyridine-cyclopropyl-CN]

and and other variables are as defined in the present invention.

In some embodiments of the present invention, the above structural unit

[Isoindolinone structure with R₁ substituent]

is selected from

[Isoindolinone structure with R₁ substituent]

and other variables are as defined in the present invention.

In some embodiments of the present invention, the above structural unit

[Isoindolinone structure with R₁ substituent]

is selected from

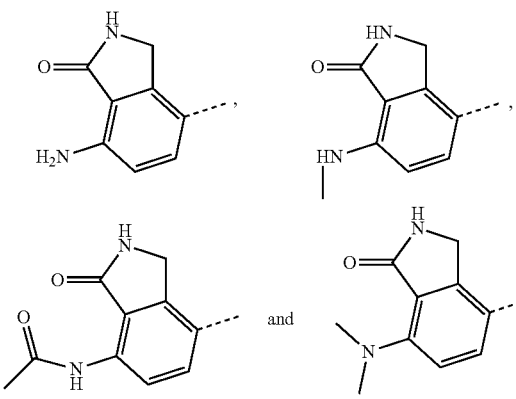

and other variables are as defined in the present invention.

In some embodiments of the present invention, the above structural unit

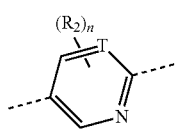

is selected from

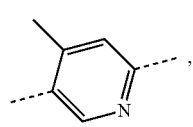

and other variables are as defined in the present invention.

There are still some embodiments of the present invention derived from any combination of the above variables.

In some embodiments of the present invention, the above compound, isomer thereof or pharmaceutically acceptable salt thereof is selected from

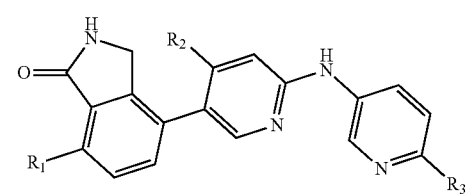

(I-1)

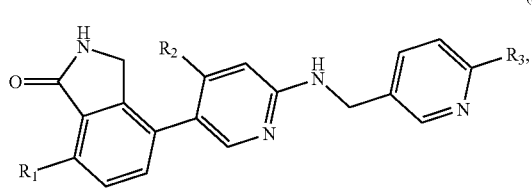

(I-2)

wherein
$R_1$, $R_2$ and $R_3$ are as defined in the present invention.

The present invention also provides a compound represented by the following formula, a isomer thereof or a pharmaceutically acceptable salt thereof, the compound is selected from

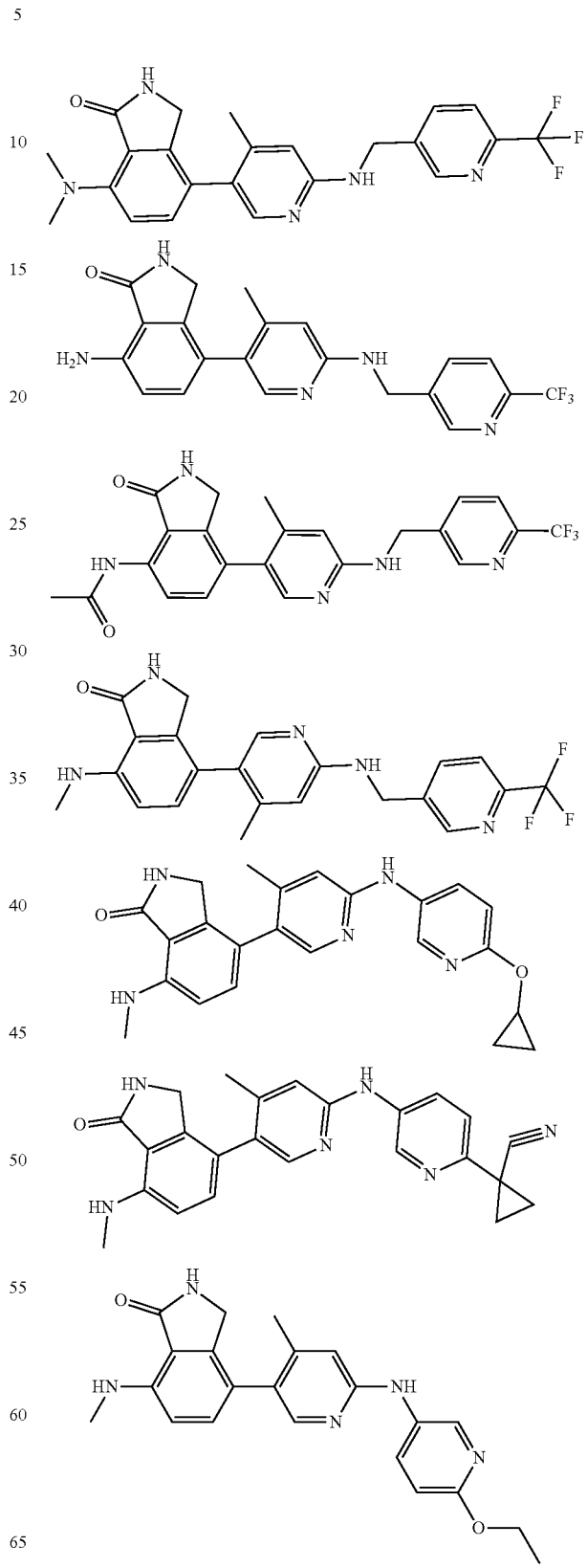

-continued
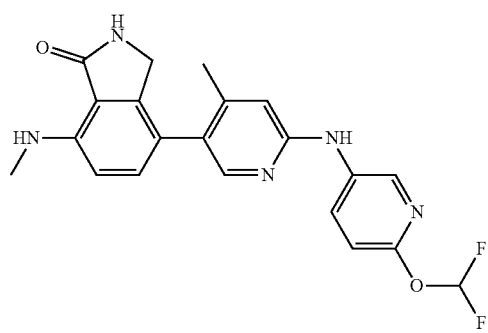
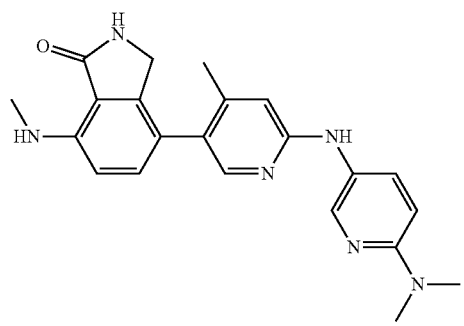
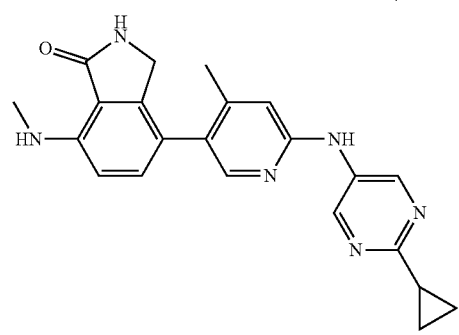
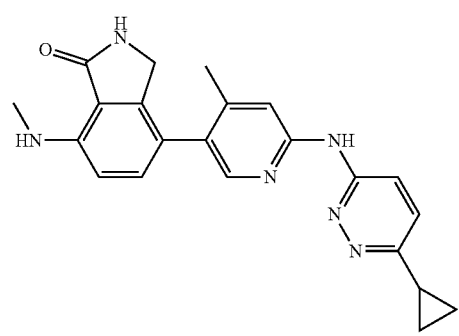
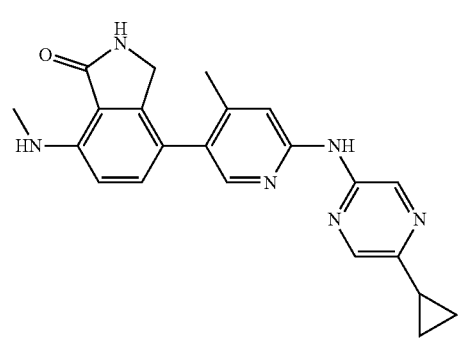
-continued
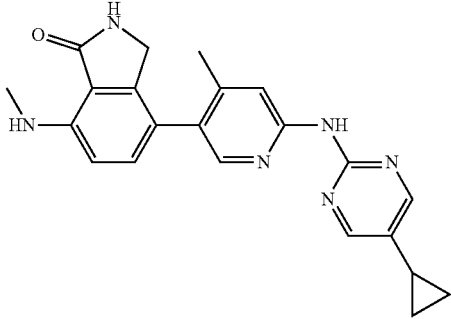
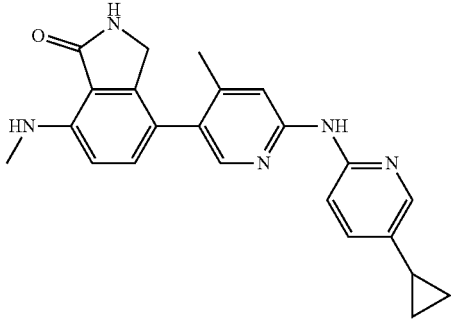
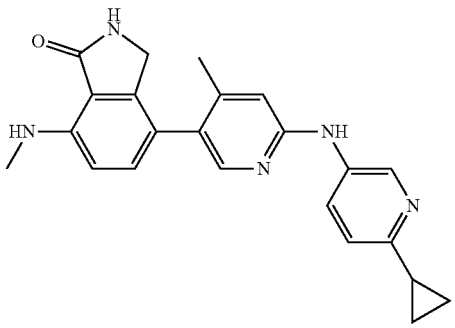
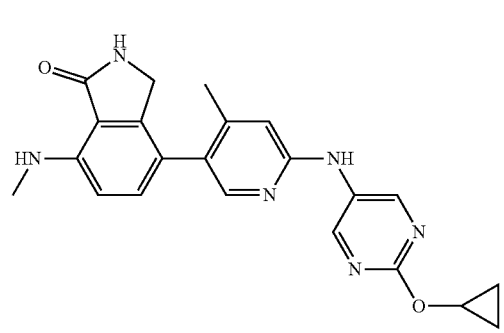
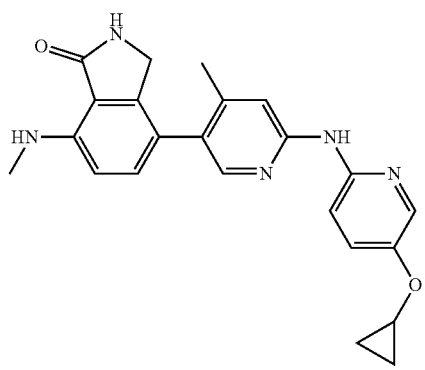

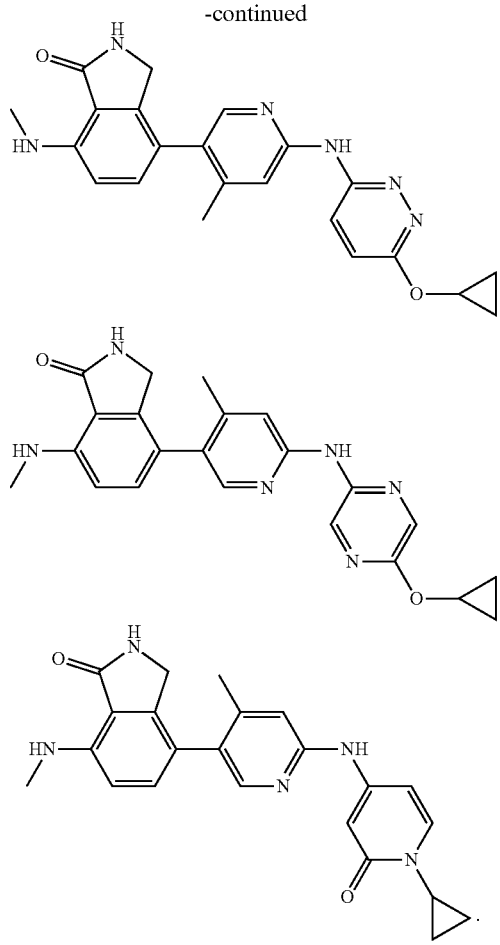

The present invention also provides a pharmaceutical composition comprising a therapeutically effective amount of the above compound or pharmaceutically acceptable salt thereof as an active ingredient and a pharmaceutically acceptable carrier.

The present invention also provides use of the above compound, isomer thereof or pharmaceutically acceptable salt thereof, or the above composition in the preparation of a medicament associated with a novel colony stimulating factor-1 receptor inhibitor.

In some embodiments of the present invention, the above medicament associated with a novel colony stimulating factor-1 receptor inhibitor is a medicament for treating tumors and autoimmune diseases.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to its corresponding trade product or its active ingredient. The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present invention, which is prepared from the compound having specific substituents found in the present invention with relatively non-toxic acids or bases. When compounds of the present invention contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present invention contain relatively basic functional groups, acid addition salts can be obtained by contacting the neutral form of such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain compounds of the present invention contain both basic and acidic functional groups so that they can be converted to any of the base or acid addition salts.

The pharmaceutically acceptable salts of the present invention can be synthesized from a parent compound containing acid radicals or bases by means of conventional chemical methods. In general, the method for preparing such salts comprises: in water or an organic solvent or a mixture of both, reacting these compounds in free acid or base forms with a stoichiometric amount of a suitable base or acid to prepare the salts.

In addition to salt forms, the compounds provided by the invention also exist in prodrug forms. The prodrugs of the compounds described herein readily undergo chemical changes under physiological conditions to be converted to the compounds of the present invention. In addition, prodrugs can be converted to the compounds of the invention by chemical or biochemical methods in the in vivo environment.

Certain compounds of the present invention may exist in unsolvated or solvated forms, including hydrated forms. Generally speaking, the solvated form is equivalent to the unsolvated form, and both are included in the scope of the present invention.

The compounds of the present invention may exist in specific geometric or stereoisomeric forms. The present invention contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present invention. Additional asymmetric carbon atoms may be present in a substituent such as an alkyl group. All these isomers and mixtures thereof are included in the scope of the present invention.

Unless otherwise stated, the term "enantiomer" or "optical isomers" refers to stereoisomers that are mirror images of each other.

Unless otherwise stated, the term "cis-trans isomer" or "geometric isomer" is caused by the fact that double bonds or single bonds of ring-forming carbon atoms cannot rotate freely.

Unless otherwise stated, the term "diastereomers" refers to stereoisomers in which molecules have two or more chiral centers and are not mirror images of each other.

Unless otherwise stated, "(D)" or "(+)" represents right-handed, "(L)" or "(−)" represents left-handed, and "(DL)" or "(±)" represents racemic.

Unless otherwise stated, the wedge-shaped solid bond (  ) and the wedge-shaped dotted bond (  ) represent the absolute configuration of a stereoscopic center; the straight solid bond (  ) and straight dotted bond (  ) represent the relative configuration of a stereoscopic center; the wavy line (  ) represents the wedge-shaped solid bond (  ) or the wedge-shaped dotted bond (  ); or the wavy line (  ) represents the straight solid bond (  ) and the straight dotted bond (  ).

The compounds of the present invention may exist in specific. Unless otherwise stated, the term "tautomer" or "tautomeric form" means that at room temperature, isomers with different functional groups are in dynamic equilibrium and can be quickly converted to each other. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Valence tautomers include some interconversions by recombination of some of bond-forming electrons. A specific example of keto-enol tautomerization is the interconversion between two tautomers, pentane-2,4-dione and 4-hydroxypent-3-en-2-one.

Unless otherwise stated, the terms "rich in one isomer", "isomer enriched", "rich in one enantiomer" or "enantiomerically enriched" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers and D and L isomers can be prepared using chiral synthesis or chiral reagents or other conventional techniques. If a particular enantiomer of a compound of the present invention is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines). The compounds of the present invention may contain unnatural proportions of atomic isotopes at one or more of the atoms constituting the compound. For example, the compounds may be radiolabeled with radioactive isotopes, such as tritium ($^3$H), iodine-125 ($^{125}$I) or C-14 ($^{14}$C). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present invention, whether radioactive or not, are intended to be encompassed within the scope of the present invention. The term "pharmaceutically acceptable carrier" refers to any formulation or carrier medium capable of delivering an effective amount of the active substance of the present invention without interfering with the biological activity of the active substance and having no toxic or side effects on the host or patient. Representative carriers include water, oil, vegetables and minerals, paste bases, lotion bases, ointment bases and the like. These bases include suspending agents, tackifiers, penetration enhancers and the like. Their formulations are well known to those skilled in the cosmetics field or topical pharmaceutical field.

The term "excipient" generally refers to the carrier, diluent and/or medium required to formulate an effective pharmaceutical composition.

For drugs or pharmacologically active agents, the term "effective amount" or "therapeutically effective amount" refers to a sufficient amount of a drug or medicament that is non-toxic but can achieve the desired effect. For the oral dosage form of the present invention, the "effective amount" of one active substance in the composition refers to the amount required to achieve the desired effect when used in combination with another active substance in the composition. The determination of the effective amount varies from person to person, depending on the age and general condition of the recipient, and also on the specific active substance. The appropriate effective amount in individual cases can be determined by those skilled in the art based on routine experiments.

The terms "active ingredient", "therapeutic agent", "active substance" or "active agent" refer to a chemical entity that can effectively treat target disorders, diseases or conditions.

"Optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom is substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2R, the group can optionally be substituted with up to two R, and R in each case has independent options. In addition, combinations of substituents and/or variants thereof are permissible only if such combinations result in stable compounds.

When the number of a linking group is 0, such as —(CRR)$_0$—, it means that the linking group is a single bond.

When one of the variables is selected from a single bond, it means that the two groups to which it is connected are directly connected. For example, when L represents a single bond in A-L-Z, it means that the structure is actually A-Z.

When a substituent is vacant, it means that the substituent does not exist. For example, when X is vacant in A-X, it means that the structure is actually A. When a substituent can be connected to more than one atom on a ring, the substituent can be bonded to any atom on the ring, for example, structural unit

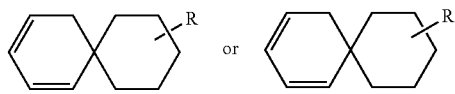

means that any position on cyclohexyl or cyclohexadiene may be substituted with the substituent R. When the substituents listed do not indicate through which atom they are connected to the substituted group, such substituents can be bonded through any of the atoms thereof, for example, pyridyl as a substituent can be attached to the substituted group via any carbon atom on the pyridine ring. When the linking group listed does not indicate the linking direction thereof, the linking direction is arbitrary, for example, the linking group L is -M-W— in

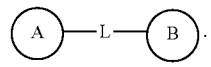

at this situation, -M-W— can connect ring A and ring B in the same direction as the reading order from left to right to form

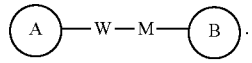

and can also connect ring A and ring B in the opposite direction as the reading order from left to right to form

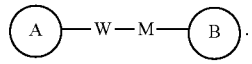

Combinations of the linking groups, substituents, and/or variants thereof permissible only if such combinations result in stable compounds.

Unless otherwise specified, the term "hetero" means a heteroatom or a heteroatomic group (i.e., an atomic groups containing a heteroatom), including atoms other than carbon (C) and hydrogen (H) as well as atomic groups containing such heteroatoms, for example, oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and optionally substituted —C(=O)N(H)—, —N(H)—, —C(=NH)—, —S(=O)$_2$N(H)— or —S(=O)N(H)—.

Unless otherwise specified, "ring" means substituted or unsubstituted cycloalkyl, heterocycloalkyl, cycloalkenyl, heterocycloalkenyl, cycloalkynyl, heterocycloalkynyl, aryl, or heteroaryl. The ring includes a single ring, bicyclic ring, a spiro ring, a ortho ring, or a bridged ring. The number of atoms in a ring is usually defined as the member number of the ring. For example, "5- to 7-membered ring" means that there are 5 to 7 atoms arranging in a circle. Unless otherwise specified, the ring optionally contains 1 to 3 heteroatoms. Therefore, "5-7 membered ring" includes, for example, phenyl, pyridyl, and piperidinyl; on the other hand, the term "5- to 7-membered heterocycloalkyl" includes pyridyl and piperidyl, but excludes phenyl. The term "ring" also includes ring systems containing at least one ring, each ring of which independently conforms to the above definition.

Unless otherwise specified, the term "heterocycle" or "heterocyclyl" means a stable monocyclic, bicyclic, or tricyclic ring containing a heteroatom or heteroatomic group, which may be saturated, partially unsaturated, or unsaturated (aromatic), and contain carbon atoms and 1, 2, 3 or 4 cycloheteroatoms independently selected from N, O and S, wherein any of the above heterocycles can be fused to a benzene ring to form a bicyclic ring. Nitrogen and sulfur heteroatoms can be optionally oxidized (i.e., NO and S(O)$_p$, p is 1 or 2). The nitrogen atom may be substituted or unsubstituted (i.e., N or NR, where R is H or other substituents that have been defined herein). The heterocycle can be attached to any heteroatom or side group of a carbon atom to form a stable structure. If the resulting compound is stable, the heterocycle described herein may be substituted at a carbon or nitrogen position. The nitrogen atom in the heterocycle is optionally quaternized. A preferred embodiment is that when the total number of S and O atoms in the heterocycle exceeds 1, these heteroatoms are not adjacent to each other. Another preferred embodiment is that the total number of S and O atoms in the heterocycle does not exceed 1. As used herein, the term "aromatic heterocyclic group" or "heteroaryl" means a stable 5, 6, 7 membered monocyclic or bicyclic aromatic ring or 7, 8, 9 or 10 membered bicyclic heterocyclic aromatic ring, which contains carbon atoms and 1, 2, 3 or 4 cycloheteroatoms independently selected from N, O and S. The nitrogen atom may be substituted or unsubstituted (i.e., N or NR, where R is H or other substituents that have been defined herein). Nitrogen and sulfur heteroatoms can be optionally oxidized (i.e., NO and S(O)$_p$, p is 1 or 2). It is worth noting that the total number of S and O atoms on the aromatic heterocycle does not exceed 1. Bridged rings are also included in the definition of heterocycle. When one or more atoms (i.e., C, O, N or S) connect two non-adjacent carbon or nitrogen atoms, a bridged ring is formed. Preferred bridged rings include, but are not limited to: one carbon atom, two carbon atoms, one nitrogen atom, two nitrogen atoms and one carbon-nitrogen group. It is worth noting that a bridge always converts a single ring into a tricyclic ring. In the bridged ring, the substituents on the ring may also appear on the bridge.

Examples of heterocyclic compounds include, but are not limited to: acridinyl, azeinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnoline decahydroquinolinyl, 2H, 6H-1,5,2-dithiazinyl, dihydrofuro [2,3-b]tetrahydrofuranyl, furanyl, furazyl, imidazolidinyl, imidazolinyl, imidazolyl, 1H-indazolyl, indolenyl, dihydroindolyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindoleyl, pyrimidinyl, phenanthridinyl, phenanthrolinyl, phenazine, phenothiazine, benzoxanthinyl, phenoxazinyl, phthalazinyl, piperazinyl, piperidinyl, piperidinonyl, 4-piperidinonyl, piperonyl, pteridinyl, purinyl, pyranyl, pyrazinyl, pyrazolidinyl, pyrazolinyl, pyrazolyl, pyridazinyl, pyridoxazole, pyridoimidazole, pyridothiazole, pyridyl, pyrrolidinyl, pyrrolinyl, 2H-pyrrolyl, pyrrolyl, quinazolinyl, quinolinyl, 4H-quinazinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthryl, thiazolyl, isothiazolylthienyl, thienoxazolyl, thienothiazolyl, thienoimidazolyl, thienyl, triazinyl, 1H-1,2,3-triazolyl, 2H-1,2,3-triazolyl, 1H-1,2,4-triazolyl, 4H-1,2,4-triazolyl and xanthenyl. Fused ring and spiro compounds are also included.

Unless otherwise specified, the term "hydrocarbyl" or its subordinate concept (such as alkyl, alkenyl, alkynyl, aryl, etc.) itself or as part of another substituent means linear, branched or cyclic hydrocarbon atomic groups or combinations thereof, which may be fully saturated (such as alkyl), mono-unsaturated or poly-unsaturated (such as alkenyl, alkynyl, aryl), may be mono-substituted or poly-substituted, may be monovalent (such as methyl), divalent (such as methylene) or polyvalent (such as methine), may include divalent or polyvalent atomic groups, and has a specified number of carbon atoms (such as $C_1$-$C_{12}$ means 1 to 12 carbon, 12 is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). "Hydrocarbyl" includes, but is not limited to, aliphatic hydrocarbyl and aromatic hydrocarbyl, and the aliphatic hydrocarbyl includes chain structure and cyclic structure, specifically including but not limited to alkyl, alkenyl, alkynyl, and the aromatic hydrocarbyl includes, but is not limited to 6-12 membered aromatic hydrocarbyl such as benzene, naphthalene, etc. In some embodiments, the term "hydrocarbyl" refers to a linear or branched atomic group or a combination thereof, which may be fully saturated, mono-unsaturated or poly-unsaturated, and may include divalent and polyvalent atomic groups. Examples of saturated hydrocarbon atomic groups include, but are not limited to, methyl, ethyl, n-propyl, isopropyl, n-butyl, tert-butyl, isobutyl, sec-butyl, isobutyl, cyclohexyl, (cyclohexyl) methyl, cyclopropylmethyl, and homologues or isomers of atomic groups such as n-pentyl, n-hexyl, n-heptyl, n-octyl, etc. Unsaturated hydrocarbyl has one or more double bonds or triple bonds, and examples thereof include, but are not limited to, vinyl, 2-propenyl, butenyl, crotonyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless otherwise specified, the term "heterohydrocarbyl" or its subordinate concept (such as heteroalkyl, heteroalkenyl, heteroalkynyl, heteroaryl, etc.) itself or in combination with another term means a stable linear, branched or cyclic hydrocarbon atomic group or a combination thereof, which is composed of a certain number of carbon atoms and at least one heteroatom. In some embodiments, the term "heteroalkyl" itself or in combination with another term means a stable linear or branched hydrocarbon atomic group or a combination thereof, which is composed of a certain number of carbon atoms and at least one heteroatom. In a typical embodiment, the heteroatom is selected from B, O, N and S, wherein the nitrogen and sulfur atoms are optionally oxidized, and the nitrogen heteroatom is optionally quaternized. Heteroatom or heteroatomic group may be located at any internal position of heterohydrocarbyl, including the positions of the hydrocarbyl to the rest of the molecule. However, the terms "alkoxy", "alkylamino" and "alkylthio" (or thioalkoxy) are used in their conventional sense and refer to those alkyl groups attached to the remainder of the molecule via an oxygen atom, an amino group, or a sulfur atom, respectively. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH=CH-O-CH_3$, $-CH_2-CH=N-OCH_3$ and $-CH=CH-N(CH_3)-CH_3$. At most two heteroatoms can be continuous, such as $-CH_2-NH-OCH_3$.

Unless otherwise specified, the term "cyclohydrocarbyl", "heterocyclohydrocarbyl" or its subordinate concepts (such as aryl, heteroaryl, cycloalkyl, heterocycloalkyl, cycloalkenyl, heterocycloalkenyl, cycloalkynyl, heterocycloalkynyl, etc.) itself or in combination with other terms means cyclized "hydrocarbyl" and "heterohydrocarbyl", respectively. In addition, as far as heterohydrocarbyl or heterocyclohydrocarbyl (such as heteroalkyl, heterocycloalkyl), heteroatoms can occupy the position where the heterocycle is attached to the rest of the molecule. Examples of cyclohydrocarbyl include, but are not limited to, cyclopentyl, cyclohexyl, 1-cyclohexenyl, 3-cyclohexenyl, cycloheptyl, and the like. Non-limiting examples of heterocyclyl include 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuran indol-3-yl, tetrahydrothiophen-2-yl, tetrahydrothiophen-3-yl, 1-piperazinyl and 2-piperazinyl.

Unless otherwise specified, the term "alkyl" is used to represent a linear or branched saturated hydrocarbyl, which may be mono-substituted (such as $-CH_2F$) or poly-substituted (such as $-CF_3$), and may be monovalent (such as methyl), divalent (such as methylene) or polyvalent (such as methine). Examples of alkyl include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl), etc.

Unless otherwise specified, "alkenyl" refers to alkyl having one or more carbon-carbon double bonds at any position on the chain, which may be mono-substituted or poly-substituted, and may be monovalent, divalent, or polyvalent. Examples of alkenyl include vinyl, propenyl, butenyl, pentenyl, hexenyl, butadienyl, piperylenyl, hexadienyl, and the like.

Unless otherwise specified, "alkynyl" refers to alkyl having one or more carbon-carbon triple bonds at any position on the chain, which may be mono-substituted or poly-substituted, and may be monovalent, divalent or polyvalent. Examples of alkynyl include ethynyl, propynyl, butynyl, pentynyl, and the like.

Unless otherwise specified, cycloalkyl includes any stable cyclic or polycyclic hydrocarbyl, in which any carbon atom is saturated, and which may be mono-substituted or poly-substituted, and may be monovalent, divalent, or polyvalent. Examples of the cycloalkyl include, but are not limited to, cyclopropyl, norbornyl, [2.2.2] bicyclooctane, [4.4.0] bicyclodecane and the like.

Unless otherwise specified, cycloalkenyl includes any stable cyclic or polycyclic hydrocarbyl containing one or more unsaturated carbon-carbon double bonds at any position on the ring, which may be mono-substituted or poly-substituted, and may be monovalent, divalent, or polyvalent. Examples of the cycloalkenyl include, but are not limited to, cyclopentenyl and cyclohexenyl.

Unless otherwise specified, cycloalkynyl includes any stable cyclic or polycyclic hydrocarbyl containing one or more carbon-carbon triple bonds at any position on the ring, which may be mono-substituted or poly-substituted, and may be monovalent, divalent, or polyvalent.

Unless otherwise specified, "cycloalkenyl alkyl" refers to alkyl substituted with cycloalkenyl.

Unless otherwise specified, "cycloalkynyl alkyl" refers to alkyl substituted with cycloalkynyl.

Unless otherwise specified, the term "halo" or "halogen" by itself or as part of another substituent means a fluorine, chlorine, bromine or iodine atom. In addition, the term "haloalkyl" is intended to include monohaloalkyl and polyhaloalkyl. For example, the term "halo($C_1$-$C_4$)alkyl" is intended to include, but is not limited to, trifluoromethyl, 2,2,2-trifluoroethyl, 4-chlorobutyl, 3-bromopropyl, and the like. Unless otherwise specified, examples of haloalkyl include, but are not limited to: trifluoromethyl, trichloromethyl, pentafluoroethyl and pentachloroethyl.

"Alkoxy" represents the above alkyl having a specific number of carbon atoms connected via an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but are not limited to: methoxy, ethoxy, n-propoxy, isopropoxy, n-butoxy, sec-butoxy, tert-butoxy, n-pentoxy and S-pentoxy.

Unless otherwise specified, the term "aryl" means a poly-unsaturated aromatic hydrocarbon substituent, which may be mono-substituted or poly-substituted, may be monovalent, divalent or polyvalent, and may be monocyclic or polycyclic (e.g., 1 to 3 rings; wherein at least one of the rings is aromatic), which are fused together or covalently linked. The term "heteroaryl" refers to aryl (or aromatic ring) containing one to four heteroatoms. In an exemplary example, the heteroatom is selected from B, N, O, and S, wherein the nitrogen and sulfur atoms are optionally oxidized, and the nitrogen atom is optionally quaternized. Heteroaryl can be connected to the remainder of the molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furyl, thienyl, pyridyl, pyrimidinyl, benzothiazolyl, purinyl, benzimidazolyl, indolyl, isoquinolinyl, quinoxalinyl, quinolinyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl and 6-quinolinyl. The substituent of any one of the above aryl and heteroaryl ring systems is selected from the acceptable substituents described below.

Unless otherwise specified, the term "5-6 membered heterocycloalkenyl" itself or in combination with other terms respectively means a partially unsaturated cyclic group consisting of 5 to 6 ring atoms and containing at least one carbon-carbon double bond, of which 1, 2, 3 or 4 ring atoms are heteroatoms independently selected from O, S and N, and the rest are carbon atoms, wherein the nitrogen atom is optionally quaternized, and the nitrogen and sulfur heteroatoms can be optionally oxidized (i.e., NO and $S(O)_p$, p is 1 or 2). It includes a single ring and a bicyclic system, wherein the bicyclic system include a spiro rings, ortho rings, and bridged rings, but any ring in this system is non-aromatic. In addition, as far as the "5-6 membered heterocycloalkenyl" is concerned, the heteroatom may occupy the connection positions of heterocycloalkenyl to the rest of the molecule. The 5-6 membered heterocyclic alkenyl includes 5-membered and 6-membered heterocyclic alkenyl and the like. Examples of 5-6 membered heterocyclic alkenyl include, but are not limited to

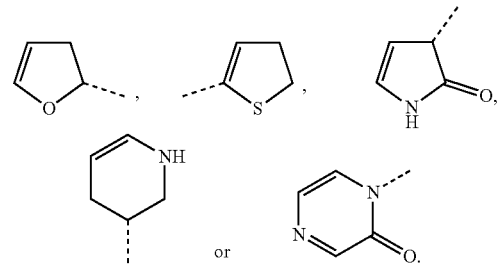

Unless otherwise specified, aryl when used in combination with other terms (e.g., aryloxy, arylthio, aralkyl) includes aryl and heteroaryl rings as defined above. Therefore, the term "aralkyl" is intended to include those atomic groups where aryl is attached to alkyl (e.g., benzyl, phenethyl, pyridylmethyl, etc.), including those alkyl in which carbon atoms (such as methylene) have been replaced by, for example, oxygen atoms, such as phenoxymethyl, 2-pyridyloxymethyl 3-(1-naphthyloxy)propyl, and the like.

The term "leaving group" refers to a functional group or atom that can be substituted by another functional group or atom through a substitution reaction (e.g., an affinity substitution reaction). For example, representative leaving groups include trifluoromethanesulfonate; chlorine, bromine and iodine; sulfonates, such as methanesulfonate, tosylate, p-bromobenzenesulfonate, and p-toluenesulfonate; and acyloxy, such as acetoxy and trifluoroacetoxy.

The term "protecting group" includes, but is not limited to, "amino protecting group", "hydroxy protecting group" or "mercapto protecting group". The term "amino protecting group" refers to a protecting group suitable for preventing side reactions occur at the nitrogen atom of an amino group. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for preventing side reactions of a hydroxyl group. Representative hydroxyl protecting groups include, but are not limited to: alkyl, such as methyl, ethyl and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TBS).

The compounds of the present invention can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present invention.

The solvents used in the present invention are commercially available. The present invention uses the following abbreviations: aq represents water; HATU represents O-(7-azabenzotriazol-1-yl)-N,N,N',N'-tetramethylurea hexafluorophosphate; EDC represents N-(3-dimethylaminopropyl atomic group)-N'-ethylcarbodiimide hydrochloride; m-CPBA represents 3-chloroperoxybenzoic acid; eq represents equivalent; CDI represents carbonyldiimidazole; DCM represents dichloromethane; PE represents petroleum ether; DIAD represents diisopropyl azodiformate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amine protecting group; BOC represents tert-butoxycarbonyl, which is an amine protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(benzenesulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide; EDCI represents 1-(3-dimethylaminopropyl)-3-ethylcarbodiimide hydrochloride; NBS represents N-bromosuccinimide; Pd$_2$(dba)$_3$ represents tris(dibenzylideneacetone) dipalladium; AIBN represents azobisisobutyronitrile; Pd(dppf)Cl$_2$ represents 1,1'-bisdiphenylphosphinoferrocene palladium dichloride; XPhos represents 2-dicyclohexylphosphino-2',4',6'-triisopropylbiphenyl; DIBAL-H represents diisobutylaluminum hydride; NaBH$_3$CN represents sodium cyanoborohydride; EGTA represents ethylene glycol bis(2-aminoethyl ether) tetraacetic acid; ACN represents acetonitrile; NMP represents N-methylpyrrolidone; Xantphos represents 4,5-bis(diphenylphosphine)-9,9-dimethylxanthene.

Compounds are named by hand or ChemDraw® software, and commercially available compounds are named by the supplier catalog names.

The compound of the present invention has significant inhibitory effect on CSF-1R kinase, and its permeability and metabolic stability are significantly improved.

DETAILED DESCRIPTION OF EMBODIMENTS

The present invention will be described in detail with the following examples, but not imply any adverse limitation to the present invention. The present invention has been described in detail herein, and the specific embodiments thereof are also disclosed therein. For a person skilled in the art, without departing from the spirit and scope of the present invention, all the variations and improvements made to the specific embodiments of the present invention would have been obvious.

Intermediate I

Synthetic Route:

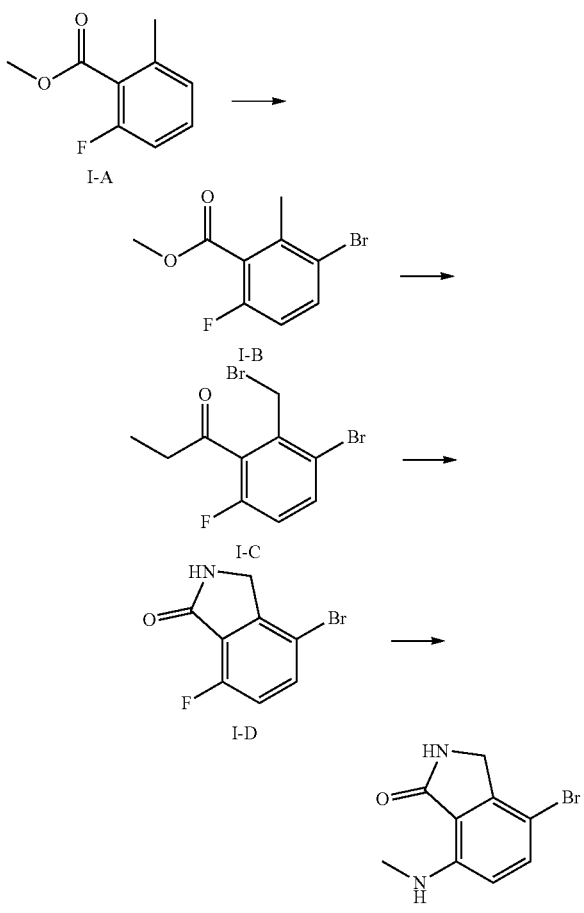

Step 1: Synthesis of Compound I-B

NBS (756.75 mg, 4.25 mmol) was added to a solution of compound I-A in H$_2$SO$_4$ (5 mL) at 0° C., and the reaction solution was stirred at 0° C. for 3 hours. The reaction solution was slowly poured into water, and extracted with EA (30 mL), washed once with saturated brine (20 mL), dried over anhydrous sodium sulfate, filtered, and concentrated. Product I-B was obtained via purification by chromatography column (PE:EA=20:1).

$^1$H NMR (400 MHz, MeOD) δ ppm 7.69 (dd, J=8.78, 5.27 Hz, 1H) 7.01 (t, J=8.91 Hz, 1H) 3.95 (s, 3H) 2.39 (s, 3H)

Step 2: Synthesis of Compound I-C

Compound I-B (6.2 g, 25.10 mmol) and NBS (5.36 g, 30.11 mmol) were dissolved in CCl$_4$ (60 mL), followed by addition of AIBN (824.16 mg, 5.02 mmol), the reaction solution was subjected to replacement with nitrogen 3 times, and stirred at 80° C. for 12 hours. The reaction solution was concentrated, and the crude product was purified by chromatography column (PE:EA=20:1) to obtain product I-C.

Step 3: Synthesis of Compound I-D

Compound I-C (0.04 g, 122.72 μmol) was dissolved in ammonia water (0.5 mL, 28% purity) and MeCN (5 mL), and the reaction solution was stirred at 25° C. for 0.5 hour. The reaction solution was concentrated, filtered, and washed with water, and the solid was collected to obtain product I-D.

MS m/z: 229.8[M+H]$^+$

Step 4: Synthesis of Compound I

Compound I-D (0.1 g, 434.72 μmol) was dissolved in methylamine (45.00 mg, 434.72 μmol, 5 mL, 30% to 34% purity) solution, and the reaction solution was stirred at 100° C. for 12 hours. The reaction solution was concentrated, and the crude product was washed with 10 mL of mixed solvent of acetonitrile and water (1:1), and filtered to obtain product I.

MS m/z: 240.8[M+H]$^+$

Intermediate II

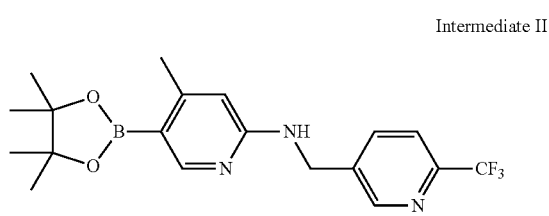 [SMILES: Cc1cc(NCc2ccc(C(F)(F)F)nc2)ncc1B1OC(C)(C)C(C)(C)O1]

Synthetic Route:

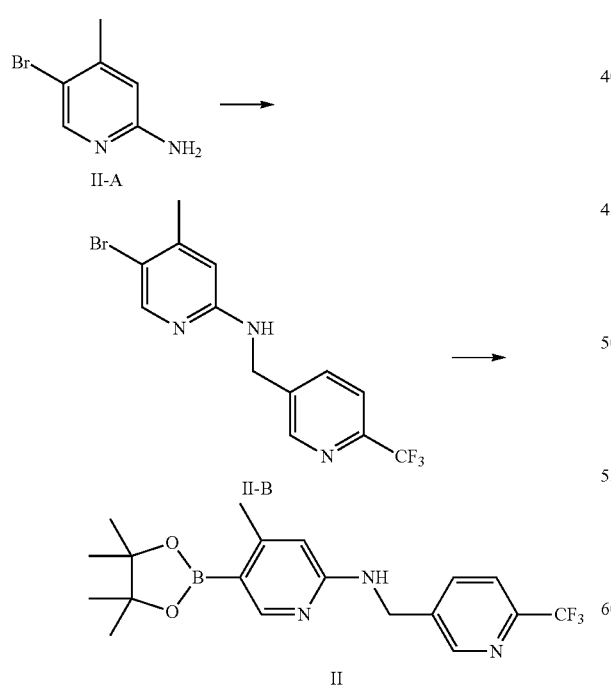

Step 1: Synthesis of Compound II-B

Compound II-A (3.00 g, 16.04 mmol) and 2-trifluoromethylpyridine-5-carbaldehyde (2.60 g, 14.85 mmol) were dissolved in acetonitrile (92.00 mL), and trifluoroacetic acid (6.91 mg, 60.60 mmol) and triethylsilane (6.75 g, 58.07 mmol) were added to the reaction system. And then the reaction solution was stirred at 93° C. for 4 hours, and concentrated under reduced pressure to obtain the crude product. The crude product was poured into an aqueous solution of potassium carbonate, and extracted with ethyl acetate (30 mL×3). The organic phases were combined and dried over anhydrous sodium sulfate. After filtering off the desiccant, the solvent was removed under reduced pressure to obtain a crude product. The crude product was purified by column chromatography (petroleum ether/ethyl acetate=8/1 to 2/1) to obtain II-B.

MS m/z: 346.1[M+H]$^+$

Step 2: Synthesis of Compound II

Under a nitrogen atmosphere, compound II-B (300.00 mg, 866.68 μmol), potassium acetate (170.11 mg, 1.73 mmol), bis(pinacolato)diboron (330.13 mg, 1.30 mmol) and Pd(dppf)Cl$_2$ (31.71 mg, 43.33 μmol) were added to a solution of 1,4-dioxane (5.00 mL), and the reaction solution was stirred under a nitrogen atmosphere at 90° C. for 14 hours, diluted with water (4 mL), and extracted with ethyl acetate (15 mL×3). The organic phases were combined, washed with saturated brine (20 mL), and dried over anhydrous sodium sulfate. After filtering off the desiccant, the solvent was removed under reduced pressure to obtain a crude product. The crude product was purified by preparative TLC (petroleum ether/ethyl acetate=3/1) to obtain II.

MS m/z: 394.1[M+H]$^+$

Intermediate III

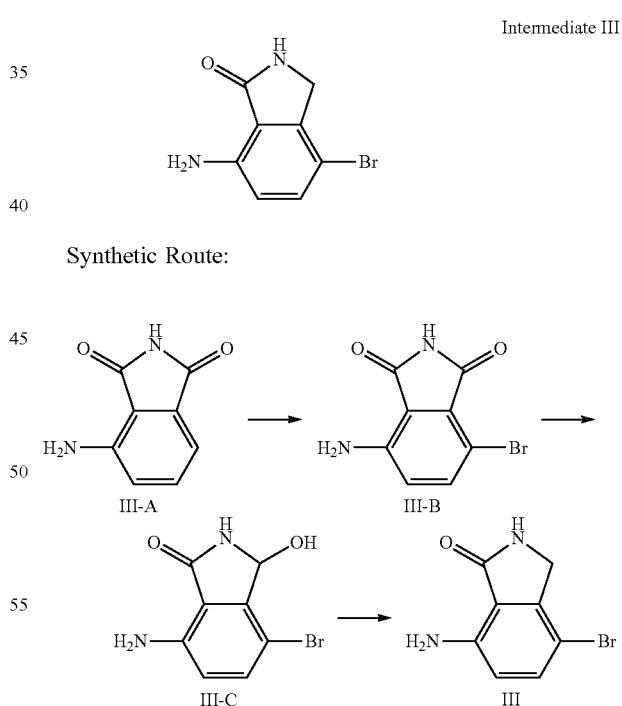

Synthetic Route:

Step 1: Synthesis of Compound III-B

Compound III-A (500.00 mg, 3.08 mmol) was placed in methanol (50.00 mL), and NBS (548.18 mg, 3.08 mmol) was added to the reaction system. The reaction solution was stirred at 28° C. for 1 hour, and filtered. The precipitated solid was collected and washed with methanol (20 mL) to finally obtain III-B.

$^1$H NMR (400 MHz, DMSO-d$_6$) δ ppm 11.10 (br s, 1H) 7.51 (d, J=8.78 Hz, 1H) 6.90 (d, J=8.78 Hz, 1H) 6.56 (br s, 2H)

Step 2: Synthesis of Compound III-C

Compound III-B (460.00 mg, 1.91 mmol) was dissolved in tetrahydrofuran (35.00 mL) and cooled to −78° C., and then DIBAL-H (1 M, 9.55 mL) was added to the reaction system and the temperature was kept at −78° C. Then the reaction solution was slowly heated to 28° C. and stirred for 1.5 hours, added with water (20 mL) under an ice water bath, and filtered through celite to remove insoluble materials. The filtrate was extracted with ethyl acetate (30 mL×3), and the organic phases were combined and dried over anhydrous sodium sulfate. After filtering off the desiccant, the solvent was removed under reduced pressure to obtain crude product III-C. The crude product could be used directly in the next reaction.

$^1$H NMR (400 MHz, DMSO-d$_6$) δ ppm 8.66 (s, 1H) 7.31 (d, J=8.53 Hz, 1H) 6.59 (d, J=8.78 Hz, 1H) 6.23 (d, J=9.54 Hz, 1H) 6.17 (s, 2H) 5.65 (d, J=9.54 Hz, 1H)

Step 3: Synthesis of Compound III

Compound III-C (170.00 mg, 699.42 μmol) was dissolved in nitromethane (7.00 mL), and then TFA (797.47 mg, 6.99 mmol) and triethylsilane (162.66 mg, 1.40 mmol) were added to the reaction system. After stirring at 28° C. for 2 hours, the reaction solution was diluted with water (10 mL), and extracted with ethyl acetate (10 mL×3). The organic phases were combined, washed with aqueous NaHCO$_3$ solution, and dried over anhydrous sodium sulfate. After filtering off the desiccant, the solvent was removed under reduced pressure to obtain product III.

$^1$H NMR (400 MHz, DMSO-d$_6$) δ ppm 8.38 (s, 1H) 7.33 (d, J=8.78 Hz, 1H) 6.56 (d, J=8.53 Hz, 1H) 6.19 (s, 2H) 4.14 (s, 2H)

Step: Synthesis of Compound IV

Compound I-D (500 mg, 2.17 mmol, 1 eq), bis(pinacolato)diboron (662.35 mg, 2.61 mmol, 1.2 eq), potassium acetate (639.96 mg, 6.52 mmol, 3 eq), and tricyclohexylphosphine (121.91 mg, 434.72 μmol, 140.93 μL, 0.2 eq) were dissolved in anhydrous dioxane (10 mL), and the reaction solution was subjected to replacement with nitrogen three times and then added with Pd$_2$(dba)$_3$ (199.04 mg, 217.36 μmol, 0.1 eq). The system was stirred at 90° C. for 3.5 hours under nitrogen protection. The reaction solution was added with 20 mL of water, extracted with DCM 40 mL (20 ml*2), and then washed with saturated brine 30 mL (30 mL*1), and dried over anhydrous sodium sulfate. After filtering off the desiccant, the filtrate was concentrated under reduced pressure to obtain a crude product. The crude product was purified by column chromatography (eluent: THF/DCM=0 to 30%) to obtain compound IV.

MS m/z: 278.0[M+H]$^+$

Example 1: Compound 1

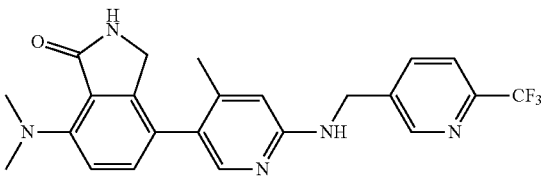 [SMILES: Cc1cc(NCc2ccc(C(F)(F)F)nc2)ncc1-c1ccc(N(C)C)c2c1CNC2=O]

Synthetic Route:

Intermediate IV

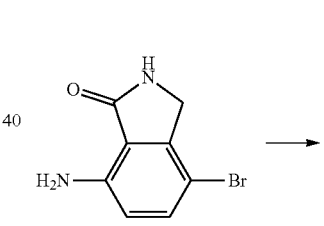

III

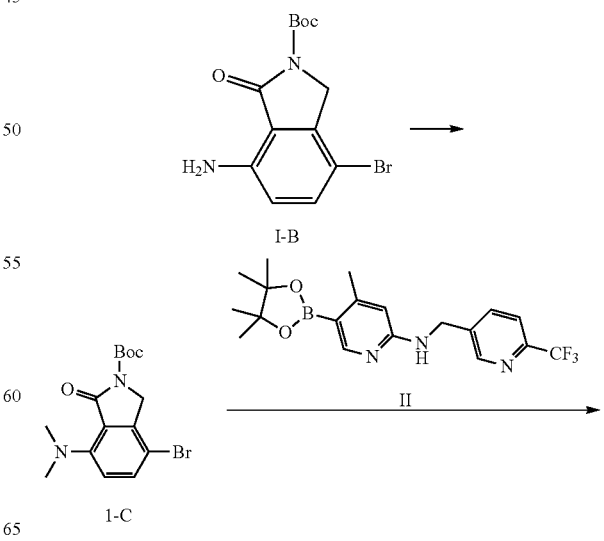

Synthetic Route:

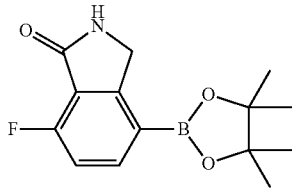

I-D

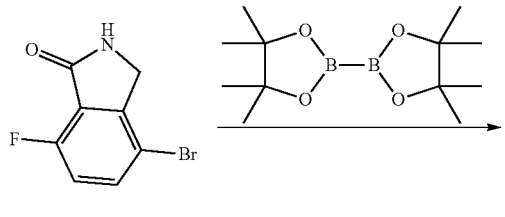

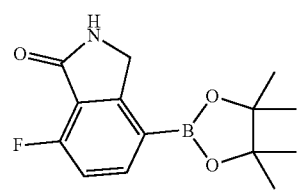

IV

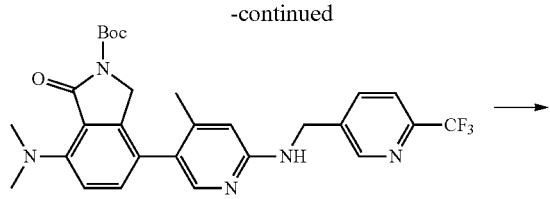

I-D

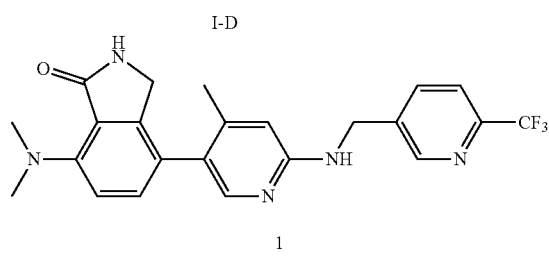

1

Step 1: Synthesis of Compound 1-B

Sodium hydrogen (52.85 mg, 1.32 mmol, 60% purity) was added to III (300.00 mg, 1.32 mmol) in THF (10.00 mL) at 0° C., and the reaction solution was stirred at 0° C. for 30 minutes. Then Boc$_2$O (288.36 mg, 1.32 mmol) was added and stirred at 0° C. for another 1 hour. The reaction solution was diluted with water (20 mL) and extract with ethyl acetate (40 mL). The organic phase was washed with saturated brine (20 mL) and dried over anhydrous sodium sulfate. After filtering off the desiccant, the solvent was removed under reduced pressure to obtain a crude product. The crude product was purified by preparative chromatography column (DCM:THF=1:1) to obtain compound 1-B.

$^1$H NMR (400 MHz, DMSO-d$_6$) δ ppm 7.41 (d, J=8.53 Hz, 1H) 6.59 (d, J=8.78 Hz, 1H) 6.49 (s, 2H) 4.45-4.55 (m, 2H) 1.49 (s, 9H)

Step 2: Synthesis of Compound 1-C

Formaldehyde (248.07 mg, 3.06 mmol, 37% purity) and sodium cyanoborohydride (96.04 mg, 1.53 mmol) were added to AcOH (10.00 mL) containing compound 1-B (100.00 mg, 305.65 μmol) at 20° C. The reaction solution was stirred at 20° C. for 12 hours. The reaction solution was diluted with water (20 mL) and extract with ethyl acetate (40 mL). The organic phase was washed with saturated brine (20 mL) and dried over anhydrous sodium sulfate. After filtering off the desiccant, the solvent was removed under reduced pressure to obtain a crude product. The crude product was purified by preparative chromatography column (petroleum ether:tetrahydrofuran=2:1) to obtain compound 1-C.

MS m/z: 355.0 [M+H]$^+$

Step 3: Synthesis of Compound 1-D

Compound 1-C (50.00 mg, 140.75 μmol), II (55.35 mg, 140.75 μmol), Pd$_2$(dba)$_3$ (25.78 mg, 28.15 μmol), Xphos (26.84 mg, 56.30 μmol) and potassium phosphate (89.63 mg, 422.25 μmol) were added to a solution of dioxane (5.00 mL) and water (500 μL), and the mixed system was degassed and purified 3 times with nitrogen. The mixed system was stirred under a nitrogen atmosphere at 85° C. for 14 hours, filtered and concentrated to obtain a crude product. The crude product was separated by preparative HPLC to obtain compound 1-D.

MS m/z: 542.3[M+H]$^+$

Step 4: Synthesis of Compound 1

Compound 1-D (20.00 mg, 36.93 μmol) was dissolved in hydrochloric acid/ethyl acetate (8 mL), and the reaction solution was stirred at 20° C. for 10 minutes, and concentrated to obtain compound 1.

MS m/z: 442.1[M+H]$^+$ $^1$H NMR (400 MHz, METHANOL-d$_4$) δ ppm 8.81 (s, 1H) 8.13 (br d, J=7.8 Hz, 1H) 8.00-7.85 (m, 3H) 7.75 (d, J=8.3 Hz, 1H) 7.15 (s, 1H) 5.49 (s, 1H) 4.84 (br s, 2H) 4.41 (s, 2H) 3.45 (s, 6H) 2.22 (s, 3H)

Example 2: Compound 2

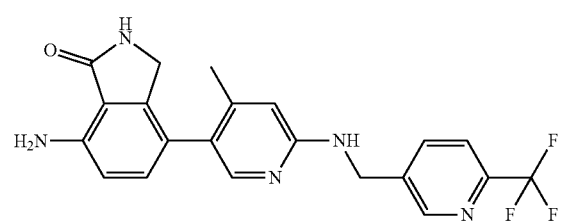 [SMILES: Cc1cc(NCc2ccc(C(F)(F)F)nc2)ncc1-c1ccc(N)c2c1CNC2=O]

Synthetic Route:

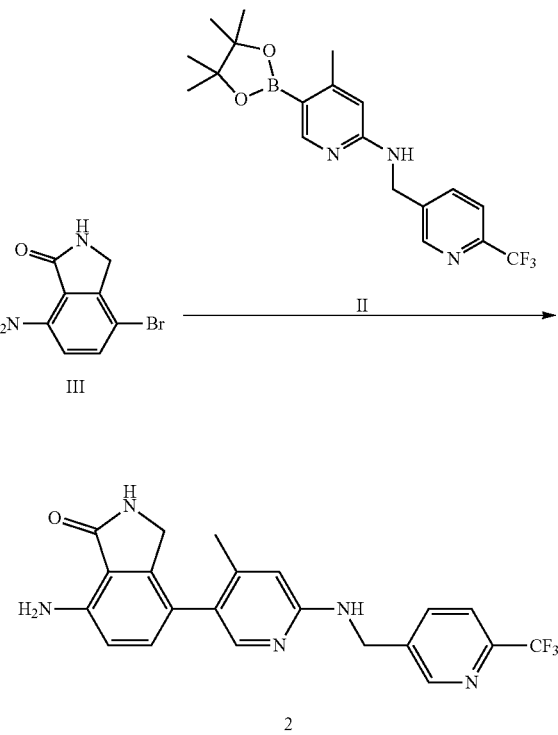

Step 1: Synthesis of Compound 2

Compound 2 was prepared with the same method as compound 1-D in example 1, except that the corresponding raw materials were used.

MS m/z: 414.0[M+H]$^+$ $^1$H NMR (400 MHz, DMSO-d$_6$) δ ppm 8.74 (s, 1H) 8.12 (s, 1H) 8.00 (br d, J=8.03 Hz, 1H) 7.86 (br d, J=8.03 Hz, 1H) 7.75 (s, 1H) 7.17 (br t, J=5.65 Hz, 1H) 6.99 (d, J=8.28 Hz, 1H) 6.59 (br d, J=8.03 Hz, 1H) 6.48 (br s, 1H) 6.09 (s, 2H) 4.61 (br d, J=5.77 Hz, 2H) 4.01 (s, 2H) 1.98 (s, 3H)

Example 3: Compound 3

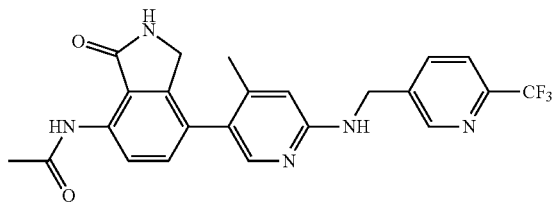 [SMILES: CC(=O)Nc1ccc(-c2cnc(NCc3ccc(C(F)(F)F)nc3)cc2C)c2c1C(=O)NC2]

Synthetic Route:

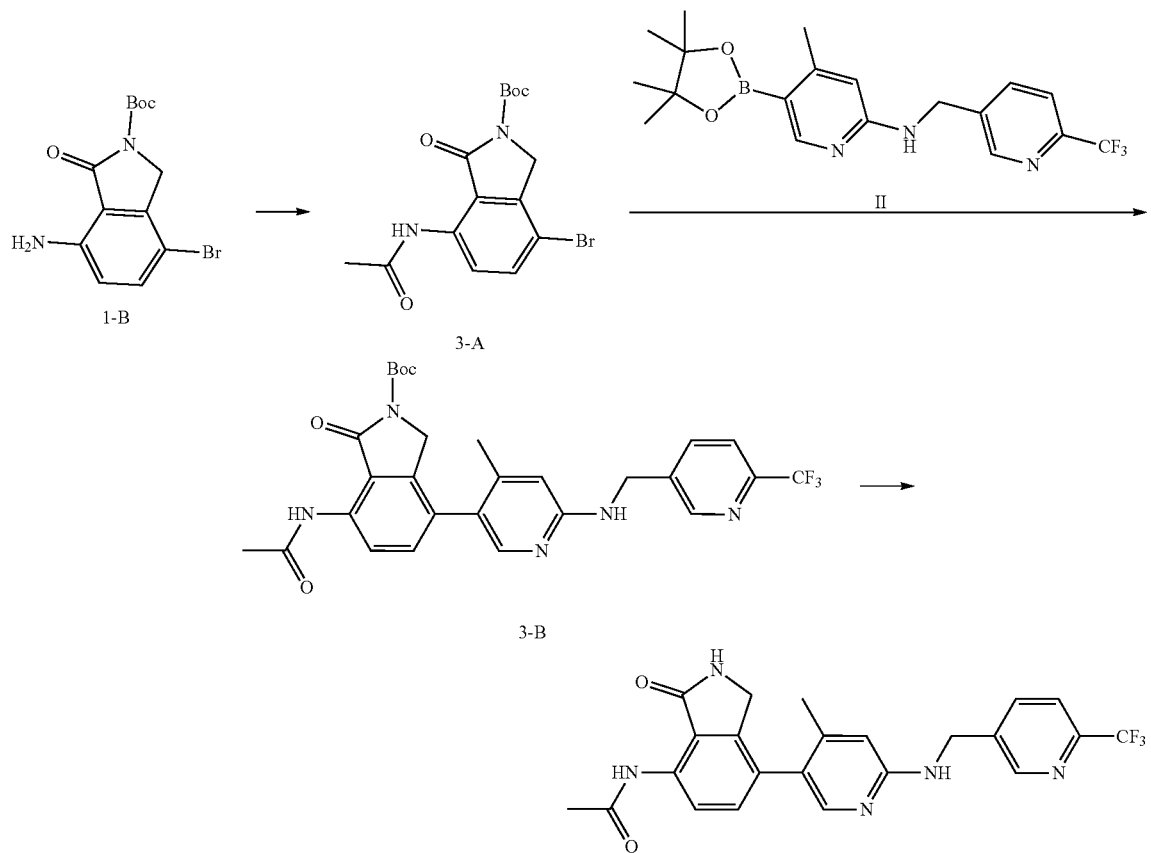

Step 1: Synthesis of Compound 3-A

Compound 1-B (100.00 mg, 305.65 μmol, 1.00 eq) and acetyl chloride (35.99 mg, 458.49 μmol, 32.72 μL, 3.00 eq) were dissolved in tetrahydrofuran (10.00 mL), and the reaction solution was stirred at 70° C. for 3 hours. The reaction solution was concentrated and purified by column chromatography (petroleum ether:ethyl acetate=4:1) to obtain product 3-A.

$^1$H NMR (400 MHz, DMSO-$d_6$) δ ppm 10.01 (s, 1H) 8.25 (d, J=8.78 Hz, 1H) 7.82 (d, J=8.78 Hz, 1H) 4.63 (s, 2H) 2.18 (s, 3H) 1.52 (s, 9H)

Step 2: Synthesis of Compound 3-B

Compound 3-B was prepared with the same method as compound 1-D in example 1, except that the corresponding raw materials were used.

MS m/z: 556.1[M+H]$^+$

Step 3: Synthesis of Compound 3

Compound 3-B (40.00 mg, 72.00 μmol) was dissolved in hydrochloric acid/ethyl acetate (5 mL), and the reaction solution was stirred at 20° C. for 10 minutes. The reaction solution was concentrated to obtain a crude product, and sodium hydroxide (10%) was added to adjust pH=9. The crude product was separated by preparative TLC (petroleum ether/ethyl acetate, 0/1) to obtain compound 3.

MS m/z: 456.0 [M+H]$^+$ $^1$H NMR (400 MHz, METHANOL-$d_4$) δ ppm 8.70 (s, 1H) 8.40 (d, J=8.0 Hz, 1H) 8.02 (br d, J=8.5 Hz, 1H) 7.77 (t, J=3.8 Hz, 2H) 7.36 (d, J=8.5 Hz, 1H) 6.56 (s, 1H) 4.69 (s, 2H) 4.21 (s, 2H) 2.19 (s, 3H) 2.06 (s, 3H)

Example 4: Compound 4

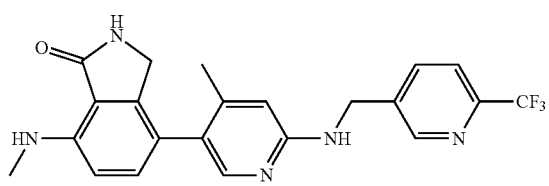 [SMILES: CNc1ccc(-c2cnc(NCc3ccc(C(F)(F)F)nc3)cc2C)c2c1C(=O)NC2]

Synthetic Route:

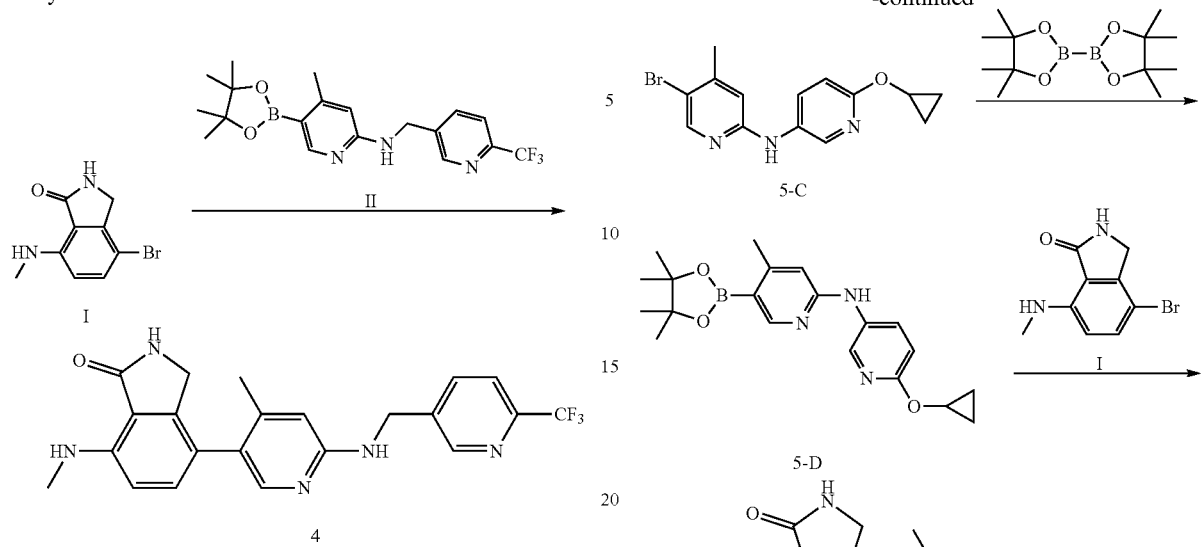

Step 1: Synthesis of Compound 4

Compound 4 was prepared with the same method as compound 1-D in example 1, except that the corresponding raw materials were used.

MS m/z: 428.2[M+H]

$^1$H NMR (400 MHz, METHANOL-d$_4$) δ ppm 8.72 (s, 1H) 8.04 (d, J=8.53 Hz, 1H) 7.79 (d, J=8.03 Hz, 1H) 7.74 (s, 1H) 7.19 (d, J=8.53 Hz, 1H) 6.66 (d, J=8.53 Hz, 1H) 6.56 (s, 1H) 4.69 (s, 2H) 4.11 (s, 2H) 2.95 (s, 3H) 2.15 (s, 3H)

Example 5: Compound 5

Synthetic Route:

Step 1: Synthesis of Compound 5-B

Compound 5-A (460 mg, 2.61 mmol, 269.01 μL) and cyclopropanol (227.71 mg, 3.92 mmol) were dissolved in NMP (1 mL), and a solution of potassium tert-butoxide in tetrahydrofuran was added dropwise slowly under an ice water bath (1 M, 3.92 mL), and then the mixture was stirred at 28° C. for 4 hours. The resulting mixture was extracted with ethyl acetate and petroleum ether (20 ml, v/v=1:1), washed with water (30 mL×1), then washed with saturated brine (30 mL), and dried over anhydrous sodium sulfate. After filtering off the desiccant, the solvent was removed under reduced pressure to obtain a crude product. The crude product was and purified by column chromatography (eluent: petroleum ether/ethyl acetate=1:0 to 40:1) to obtain compound 5-B.

MS m/z: 213.9[M+H]$^+$ $^1$H NMR (400 MHz, DMSO-d$_6$) δ ppm 8.31 (d, J=2.51 Hz, 1H) 7.92 (dd, J=8.78, 2.51 Hz, 1H) 6.87 (d, J=8.78 Hz, 1H) 4.16 (tt, J=6.21, 3.07 Hz, 1H) 0.73-0.79 (m, 2H) 0.64-0.69 (m, 2H)

Step 2: Synthesis of Compound 5-C

Compound 5-B (170 mg, 794.17 μmol), 5-bromo-4-methyl-2-aminopyridine (148.54 mg, 794.17 μmol), cesium carbonate (776.27 mg, 2.38 mmol), Xantphos (91.90 mg, 158.83 μmol) and palladium acetate (17.83 mg, 79.42 μmol) were dissolved in anhydrous 1,4 dioxane (2 ml), and the reaction solution was reacted at 100° C. for 15 hours under nitrogen protection. The reaction solution was filtered through celite, and then the filtrate was depressurized and concentrated to obtain a crude product. The crude product was purified by preparative TLC (developing solvent:petroleum ether/ethyl acetate=4:1) to obtain compound 5-C.

MS m/z: 319.8[M+H]$^+$

Step 3: Synthesis of Compound 5-D

Compound 5-C (200 mg, 624.64 µmol), bis(pinacolato)diboron (237.93 mg, 936.96 µmol), potassium acetate (153.26 mg, 1.56 mmol), and tricyclohexylphosphine (17.52 mg, 62.46 µmol) were dissolved in anhydrous 1,4-dioxane (8 mL). The reaction solution was stirred, subjected to replacement with nitrogen three times, then added with Pd$_2$(dba)$_3$ (28.60 mg, 31.23 µmol), and stirred at 90° C. for 12 hours under nitrogen protection. The reaction solution was diluted with 20 ml of ethyl acetate, and then filtered through celite, and the filtrate was concentrated to obtain a crude product. The crude product was purified by column chromatography (eluent: petroleum ether/tetrahydrofuran=10:1 to 6:1) to obtain compound 5-D.

MS m/z: 368.2[M+H]$^+$

Step 4: Synthesis of Compound 5

Compound 5-D (99 mg, 269.57 µmol), compound I (54.16 mg, 224.64 µmol), anhydrous potassium phosphate (143.05 mg, 673.93 µmol), Xphos (21.42 mg, 44.93 µmol) were dissolved in anhydrous 1,4-In dioxane (2 ml) and water (0.2 ml). The reaction solution was subjected to replacement with nitrogen three times, then added with Pd$_2$(dba)$_3$ (20.57 mg, 22.46 µmol), and reacted under microwave at 110° C. for 10 minutes. The reaction solution was diluted with 20 ml of ethyl acetate, and then filtered through celite, and the filtrate was concentrated to obtain a crude product. The crude product was purified by preparative HPLC (neutral, acetonitrile, water) to obtain compound 5.

MS m/z: 402.2[M+H]$^+$ $^1$H NMR (400 MHz, DMSO-d$_6$) δ ppm 8.93 (s, 1H) 8.41 (d, J=2.51 Hz, 1H) 8.23 (s, 1H) 8.05 (dd, J=8.92, 2.89 Hz, 1H) 7.92 (s, 1H) 7.17 (d, J=8.28 Hz, 1H) 6.82 (d, J=8.78 Hz, 1H) 6.67-6.72 (m, 2H) 6.56-6.61 (m, 1H) 4.13 (tt, J=6.12, 3.04 Hz, 1H) 4.07 (s, 2H) 2.87 (d, J=5.02 Hz, 3H) 2.06 (s, 3H) 0.72-0.75 (m, 2H) 0.64 (br s, 2H)

Example 6: Compound 6

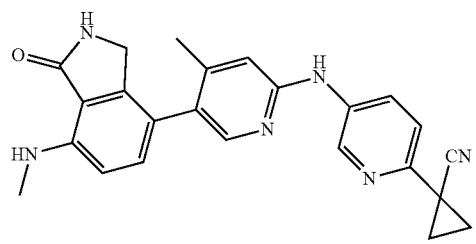 [SMILES: CNc1ccc(-c2cnc(Nc3ccc(C4(C#N)CC4)nc3)cc2C)c2c1C(=O)NC2]

Synthetic Route:

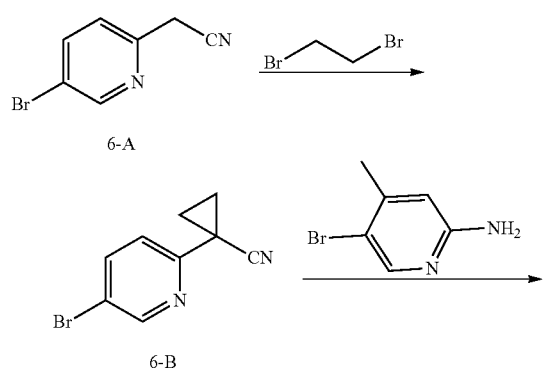

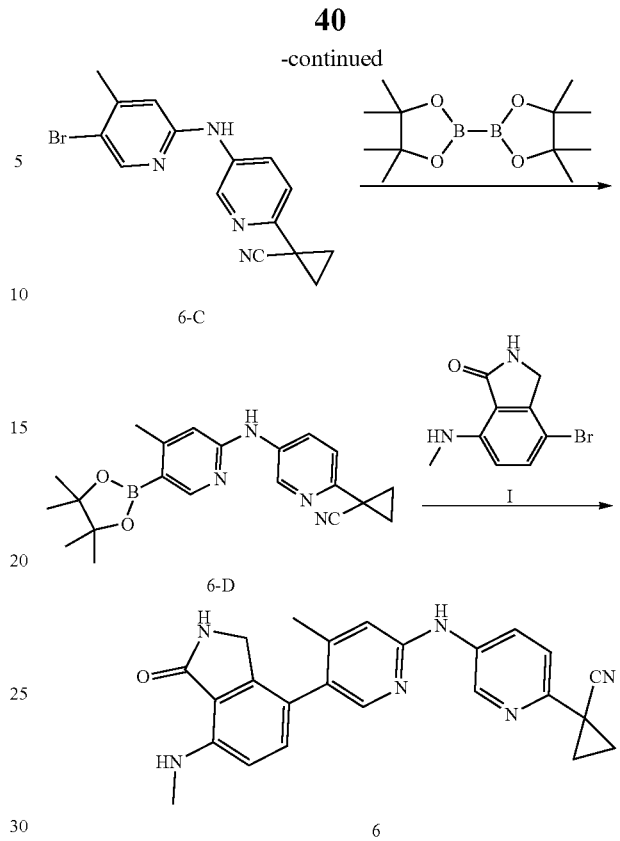

Step 1: Synthesis of Compound 6-B

Compound 6-A ((500 mg, 2.54 mmol), 1,2-dibromoethane (953.46 mg, 5.08 mmol), and tetrabutylammonium bromide (818.06 mg, 2.54 mmol) were dissolved in acetonitrile (10 mL). The reaction system was then added with 12.5 ml of sodium hydroxide aqueous solution (50%), and stirred at 19° C. for 2 hours. The reaction solution was added with 30 ml of water, extracted with 30 ml of ethyl acetate, then washed with 30 ml of saturated brine, and dried over anhydrous sodium sulfate. After filtering off the desiccant, the solvent was removed under reduced pressure to obtain a crude product. The crude product was purified by column chromatography (eluent: petroleum ether/ethyl acetate=10:1) to obtain compound 6-B.

MS m/z: 222.8[M+H]$^+$

Step 2: Synthesis of Compound 6-C

Compound 6-C was prepared with the same method as compound 5-C in example 5, except that the corresponding raw materials were used.

MS m/z: 329.0[M+H]$^+$

Step 3: Synthesis of Compound 6-D

Compound 6-D was prepared with the same method as compound 5-D in example 5, except that the corresponding raw materials were used.

MS m/z: 377.1[M+H]$^+$

Step 4: Synthesis of Compound 6

Compound 6 was prepared with the same method as compound 5 in example 5, except that the corresponding raw materials were used.

MS m/z: 411.1[M+H]$^+$ $^1$H NMR (400 MHz, DMSO-d$_6$) δ ppm 9.30 (s, 1H) 8.74 (d, J=2.51 Hz, 1H) 8.23-8.27 (m, 2H) 7.99 (s, 1H) 7.45 (d, J=8.78 Hz, 1H) 7.19 (d, J=8.28 Hz, 1H) 6.78 (s, 1H) 6.71 (br d, J=5.02 Hz, 1H) 6.60 (d, J=8.53 Hz, 1H) 4.08 (s, 2H) 2.87 (d, J=5.02 Hz, 3H) 2.08 (s, 3H) 1.70-1.74 (m, 2H) 1.59-1.63 (m, 2H)

Example 7: Compound 7

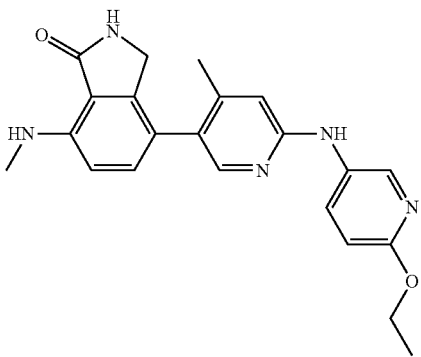 [SMILES: CCOc1ccc(Nc2cc(C)c(-c3ccc(NC)c4c3CNC4=O)cn2)cn1]

Synthetic Route:

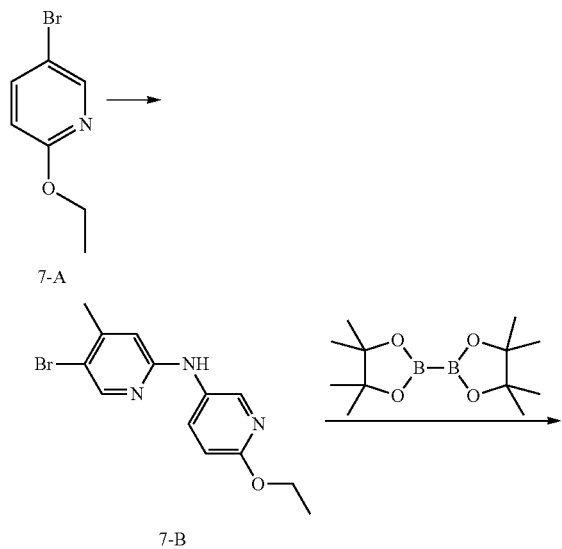

Step 1: Synthesis of Compound 7-B

Compound 7-B was prepared with the same method as compound 5-C in example 5, except that the corresponding raw materials were used.

MS m/z: 307.8[M+H]+

Step 2: Synthesis of Compound 7-C

Compound 7-C was prepared with the same method as compound 5-D in example 5, except that the corresponding raw materials were used.

MS m/z: 356.2[M+H]+

Step 3: Synthesis of Compound 7

Compound 7 was prepared with the same method as compound 5 in example 5, except that the corresponding raw materials were used.

MS m/z: 390.0[M+H]+

1H NMR (400 MHz, DMSO-d$_6$) δ ppm 8.87 (s, 1H), 8.38 (d, J=2.0 Hz, 1H), 8.22 (s, 1H), 8.01 (dd, J=3.0, 9.0 Hz, 1H), 7.91 (s, 1H), 7.17 (d, J=9.0 Hz, 1H), 6.77-6.65 (m, 3H), 6.59 (d, J=9.0 Hz, 1H), 4.24 (q, J=7.0 Hz, 2H), 4.07 (s, 2H), 2.87 (d, J=5.0 Hz, 3H), 2.05 (s, 3H), 1.30 (t, J=7.0 Hz, 3H)

Example 8: Compound 8

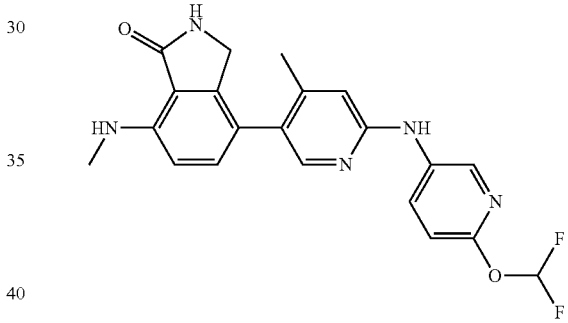

Synthetic Route:

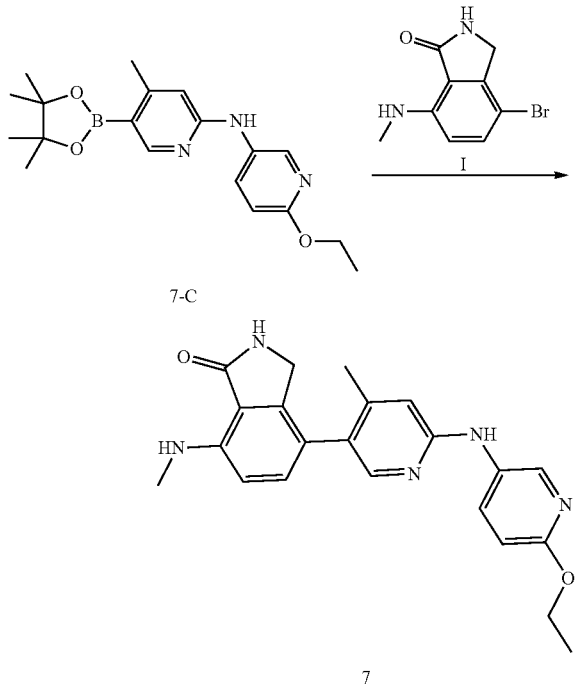

43

-continued

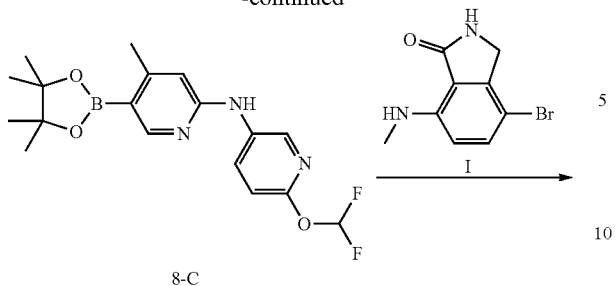

8-C

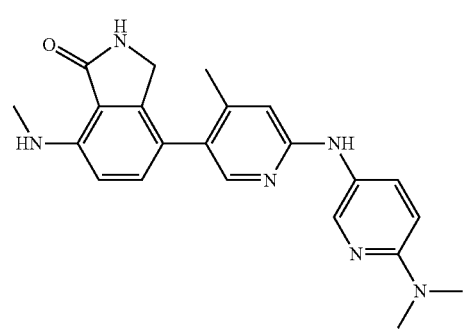

8

Step 1: Synthesis of Compound 8-B

Compound 8-B was prepared with the same method as compound 5-C in example 5, except that the corresponding raw materials were used.

MS m/z: 329.8[M+H]+

$^1$H NMR (400 MHz, CHLOROFORM-d) δ ppm 8.23-8.18 (m, 2H), 7.90 (dd, J=2.8, 8.8 Hz, 1H), 7.40 (t, J=73.2 Hz, 1H), 6.92 (d, J=8.4 Hz, 1H), 6.58 (s, 1H) 6.34 (br s, 1H), 2.33 (s, 3H)

Step 2: Synthesis of Compound 8-C

Compound 8-C was prepared with the same method as compound 5-D in example 5, except that the corresponding raw materials were used.

MS m/z: 378.2 [M+H]+

Step 3: Synthesis of Compound 8

Compound 8 was prepared with the same method as compound 5 in example 5, except that the corresponding raw materials were used.

MS m/z: 412.0 [M+H]+

1H NMR (400 MHz, METHANOL-d$_4$) δ ppm 8.44 (d, J=2.0 Hz, 1H), 8.15 (dd, J=2.4, 8.4 Hz, 1H), 7.94-7.82 (m, 1H), 7.61-7.36 (m, 1H), 7.23 (d, J=8.0 Hz, 1H), 6.93 (d, J=9.0 Hz, 1H), 6.76 (s, 1H), 6.68 (d, J=8.0 Hz, 1H), 4.15 (s, 2H), 2.97 (s, 3H), 2.13 (s, 3H)

44

Example 9: Compound 9

Synthetic Route:

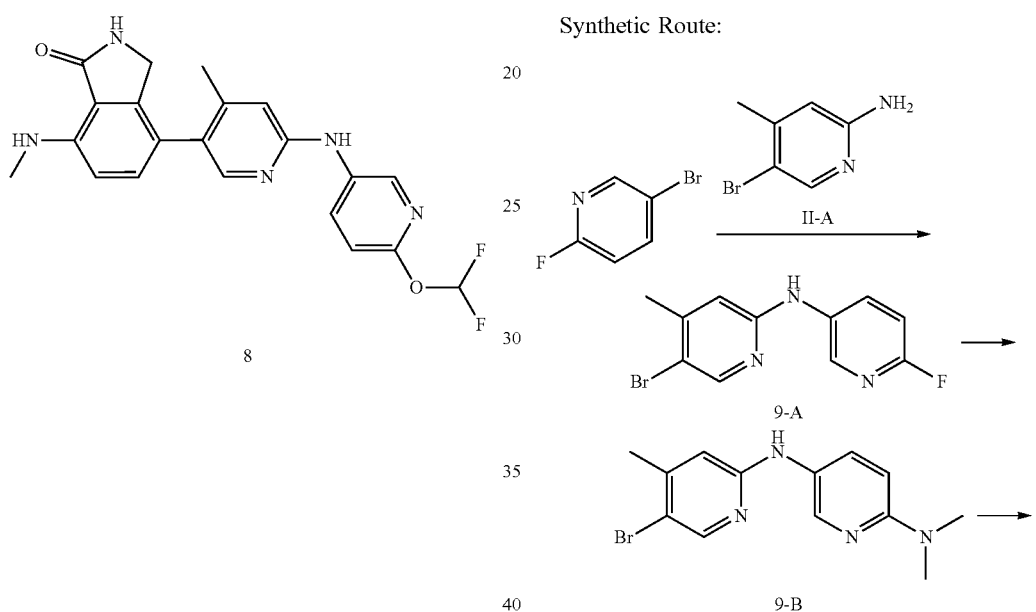

Step 1: Synthesis of Compound 9-A

Compound 2-fluoro-5 bromopyridine (200 mg, 1.14 mmol), compound II-A (212.56 mg, 1.14 mmol), and cesium carbonate (1.11 g, 3.41 mmol), 4,5-bisdiphenylphosphine-9,9-dimethylxanthene (131.51 mg, 227.29 μmol) were dissolved in anhydrous 1,4-dioxane (5 ml). The reaction solution was stirred, subjected to replacement with nitrogen three times, then added with palladium acetate (25.51 mg, 113.65 µmol), and stirred for 12 hours at 100° C. under nitrogen protection. The reaction solution was added with 30 ml of water, extracted with 30 ml of ethyl acetate, then washed with 20 ml of saturated brine, and dried over anhydrous sodium sulfate. After filtering off the desiccant, the solvent was removed under reduced pressure to obtain a crude product. The crude product was purified by column chromatography (eluent: petroleum ether/ethyl acetate=7:1 to 4:1) to obtain compound 9-A.

MS m/z: 281.9 [M+H]⁺

Step 2: Synthesis of Compound 9-B

Compound 9-A (100 mg, 354.47 µmol) was dissolved in an aqueous solution of dimethylamine (10 ml, 33%), and the reaction solution was sealed at 130° C. and stirred for 12 hours. The reaction solution was added with 5 ml of water, filtered and suction-dried to obtain a crude product. The crude product was washed with 3 ml of water, filtered and suction-dried to obtain compound 9-B.

MS m/z: 306.9 [M+H]⁺

Step 3: Synthesis of Compound 9-C

Compound 9-C was prepared with the same method as compound 5-D in example 5, except that the corresponding raw materials were used.

MS m/z: 354.9 [M+H]⁺

Step 4: Synthesis of Compound 9

Compound 9 was prepared with the same method as compound 5 in example 5, except that the corresponding raw materials were used.

MS m/z: 389.1 [M+H]+

1H NMR (400 MHz, METHANOL-d₄) δ ppm 8.22 (s, 1H), 8.09 (br d, J=9.3 Hz, 1H), 7.96 (s, 1H), 7.62 (br d, J=8.0 Hz, 1H), 7.49-7.40 (m, 2H), 7.26 (s, 1H), 4.38 (br s, 2H), 3.40 (s, 6H), 3.17 (s, 3H), 2.30 (s, 3H)

Example 10: Compound 10

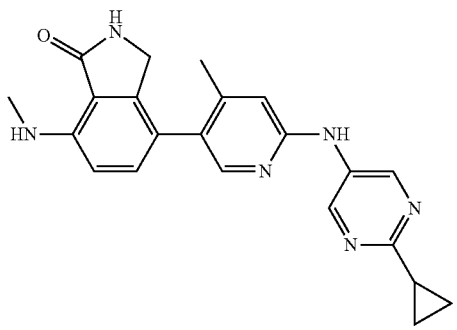 [SMILES: CNc1ccc(-c2cnc(Nc3cnc(C4CC4)nc3)cc2C)c2c1C(=O)NC2]

Synthetic Route:

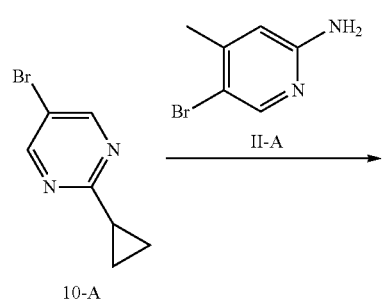

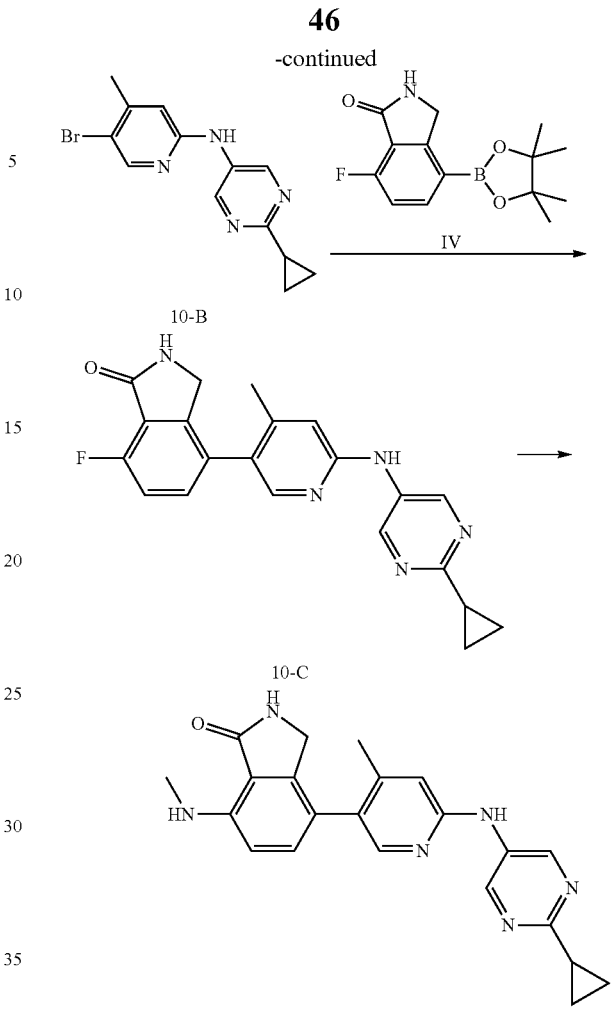

Step 1: Synthesis of Compound 10-B

Compound 10-A (500 mg, 2.51 mmol), 1-1 (469.83 mg, 2.51 mmol), cesium carbonate (2.46 g, 7.54 mmol, 3 eq) and Xantphos (290.69 mg, 502.39 µmol) were dissolved in anhydrous dioxane (8 mL). The reaction solution was subjected to replacement with nitrogen three times, then added with palladium acetate (56.40 mg, 251.20 µmol), and stirred for 5 hours at 100° C. under nitrogen protection. The reaction solution was added with water (40 ml), extracted with EA (40 ml), washed with saturated brine (30 ml), dried over anhydrous sodium sulfate, and filtered. The filtrate was concentrated under reduced pressure to obtain a crude product. The crude product was purified by column chromatography (eluent: THF/PE=0 to 50%) to obtain compound 10-B.

MS m/z: 304.8[M+H]⁺

Step 2: Synthesis of Compound 10-C

Compound 10-B (300 mg, 983.05 µmol), 1-2 (272.40 mg, 983.05 µmol), anhydrous potassium phosphate (626.02 mg, 2.95 mmol), and XPhos (93.73 mg, 196.61 µmol) were dissolved in anhydrous dioxane (15 ml) and water (1.5 ml). The reaction solution was subjected to replacement with nitrogen three times, then added with Pd₂(dba)₃ (90.02 mg, 98.31 µmol), and stirred at 100° C. for 3 hours under nitrogen protection. The reaction solution was concentrated under reduced pressure to obtain a crude product. The crude product was purified by column chromatography (eluent: DCM:THF (NH₃.H₂O, 1%)=4:1 to 1:1) to obtain compound 10-C.

MS m/z: 376.0[M+H]⁺

Step 3: Synthesis of Compound 10

Compound 10-C (323 mg, 860.42 μmol, 1 eq) was dissolved in a solution of methylamine in ethanol (5.52 mg, 53.28 μmol, 5 mL, 30% purity), and the reaction solution was stirred at 100° C. for 12 hours, and concentrated under reduced pressure to obtain a crude product. The crude product was washed with acetonitrile (5 ml) and then with acetonitrile (4 ml) to obtain the compound. The obtained compound was dissolved in ethyl acetate (5 mL), and then HCl/EtOAc (2 mL) was added dropwise. The system was stirred at 16° C. for 20 minutes, and the reaction solution was concentrated under reduced pressure to obtain a crude product. The crude product was washed with acetonitrile (4 ml) to obtain compound 10.

MS m/z: 386.9[M+H]$^+$

1H NMR (400 MHz, DMSO-d6) δ ppm 9.76 (br s, 1H), 8.97 (s, 2H), 8.27 (s, 1H), 7.99 (s, 1H), 7.20 (d, J=8.3 Hz, 1H), 6.90 (s, 1H), 6.60 (d, J=8.3 Hz, 1H), 4.08 (s, 2H), 2.87 (s, 3H), 2.22-2.17 (m, 1H), 2.11 (s, 3H), 1.05-0.95 (m, 4H)

Example 11: Compound 11

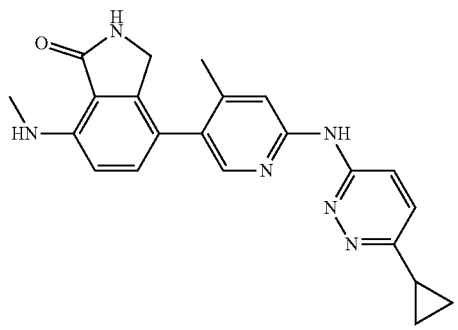

Synthetic Route:

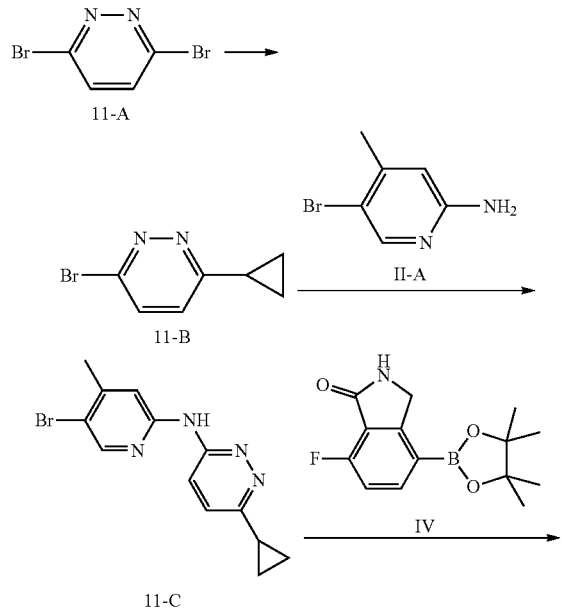

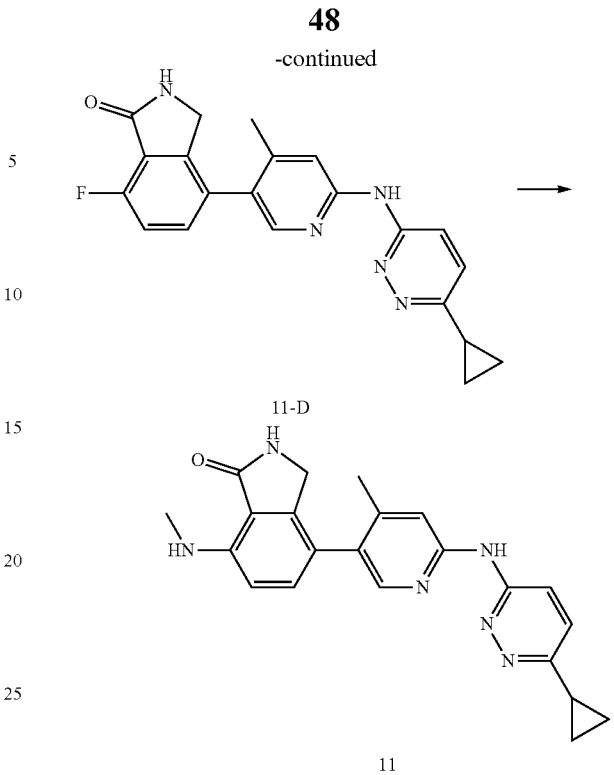

Step 1: Synthesis of Compound 11-B

Cyclopropylboronic acid (1 g, 11.64 mmol) was dissolved in water (5 mL) and toluene (50 mL), and II-A (3.32 g, 13.97 mmol) and cesium carbonate (11.38 g, 34.93 mmol) were added. The reaction solution was subjected to replacement with nitrogen three times, added with Pd(dppf)Cl$_2$-DCM (950.72 mg, 1.16 mmol), and stirred for 3 hours at 120° C. under nitrogen protection. And then the reaction solution was extracted with ethyl acetate (50 mL). The organic phase was collected, washed with saturated brine (50 mL), dried over anhydrous sodium sulfate, and concentrated to obtain a crude product, which is separated and purified by chromatography column (SiO$_2$, petroleum ether/ethyl acetate=1:1) to obtain compound 11-B.

MS m/z: 200.8[M+H]$^+$ $^1$H NMR (400 MHz, CHLOROFORM-d) δ ppm 7.47 (d, J=8.8 Hz, 1H), 7.10 (d, J=8.8 Hz, 1H), 2.11 (tt, J=5.2, 8.0 Hz, 1H), 1.21-1.13 (m, 4H)

Step 2: Synthesis of Compound 11-C

Compound 11-C was prepared with the same method as compound 5-C in example 5, except that the corresponding raw materials were used.

MS m/z: 304.8[M+H]$^+$

Step 3: Synthesis of Compound 11-D

Compound 11-D was prepared with the same method as compound 5 in example 5, except that the corresponding raw materials were used.

MS m/z: 376.0[M+H]$^+$

Step 4: Synthesis of Compound 11

Compound 11-D was prepared with the same method as compound 5 in example 5, except that the corresponding raw materials were used.

Compound 11-D (120 mg, 319.66 μmol) was dissolved in a methylamine/ethanol solution (33.09 mg, 319.66 μmol, 15 mL, 30% purity). The resulting reaction solution was reacted at 100° C. for 12 hours in a tank, and then concentrated to obtain a crude product. The crude product was prepared and separated [water (0.05% HCl)-ACN] to obtain compound 11.

MS m/z: 387.0[M+H]$^+$

1H NMR (400 MHz, METHANOL-d$_4$) δ ppm 8.32 (br s, 1H), 7.91 (br s, 1H), 7.77 (br s, 1H), 7.40 (d, J=8.3 Hz, 1H), 7.33 (br s, 1H), 6.97 (d, J=8.5 Hz, 1H), 4.23 (s, 2H), 3.04 (s, 3H), 2.66 (s, 1H), 2.32 (br s, 3H), 1.28 (br d, J=7.8 Hz, 2H), 1.18 (br d, J=3.8 Hz, 2H)

Example 12: Compound 12

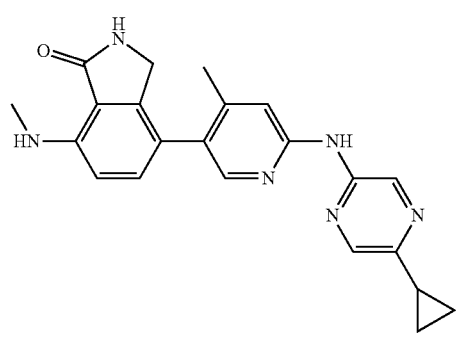 [SMILES: CNc1ccc(-c2cnc(Nc3cnc(C4CC4)cn3)cc2C)c2c1C(=O)NC2]

Synthetic Route:

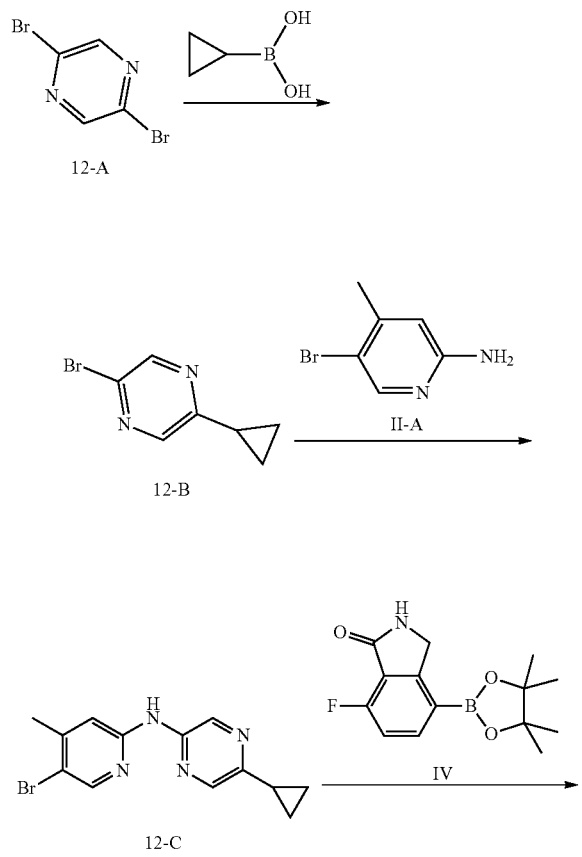

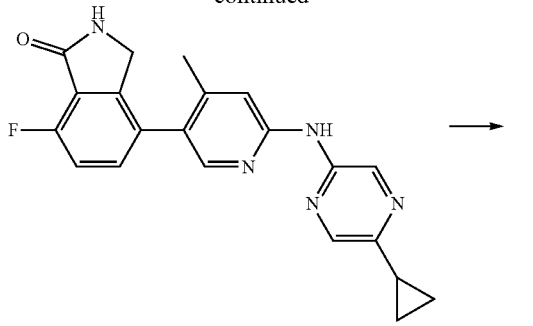

12-D

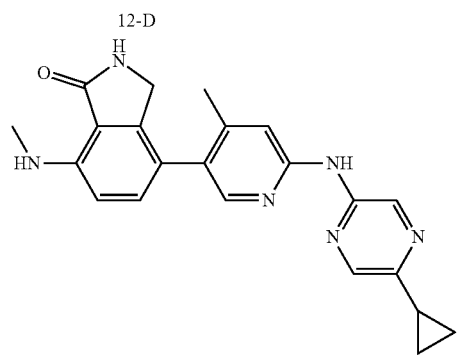

12

Step 1: Synthesis of Compound 12-B

Compound 12-A (2 g, 8.41 mmol), cyclopropylboronic acid (866.63 mg, 10.09 mmol), and cesium carbonate (8.22 g, 25.22 mmol) were dissolved in anhydrous toluene (90 mL) and water (9 mL). The reaction solution was subjected to replacement with nitrogen three times, added with Pd(dppf)Cl$_2$ (615.19 mg, 840.76 μmol), and stirred at 100° C. for 4 hours under nitrogen protection. The reaction solution was added with water (50 ml), extracted with EA (40 ml), washed with saturated brine (40 ml), dried over anhydrous sodium sulfate, and filtered. The filtrate was concentrated under reduced pressure to obtain a crude product. The crude product was purified by column chromatography (eluent: PE:EA=60/1) to obtain compound 12-B.

MS m/z: 198.8[M+H]$^+$

Step 2: Synthesis of Compound 12-C

Compound 12-C was prepared with the same method as compound 5-C in example 5, except that the corresponding raw materials were used.

MS m/z: 304.9[M+H]$^+$

Step 3: Synthesis of Compound 12-D

Compound 12-D was prepared with the same method as compound 5 in example 5, except that the corresponding raw materials were used.

MS m/z: 376.0[M+H]$^+$

Step 4: Synthesis of Compound 12

Compound 12 was prepared with the same method as compound 10 in example 10, except that the corresponding raw materials were used.

MS m/z: 387.0[M+H]$^+$

1H NMR (400 MHz, METHANOL-d$_4$) δ ppm 8.41 (s, 1H), 8.37 (d, J=1.3 Hz, 1H), 8.13 (s, 1H), 7.41 (d, J=8.3 Hz, 1H), 7.36 (s, 1H), 6.92 (d, J=8.5 Hz, 1H), 4.25 (s, 2H), 3.02 (s, 3H), 2.36 (s, 3H), 2.25-2.18 (m, 1H), 1.11-1.01 (m, 4H)

Example 13: Compound 13

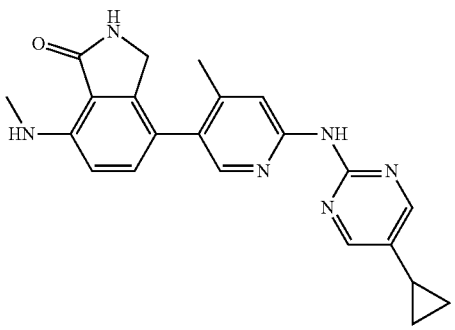 [SMILES: CNc1ccc(-c2cnc(Nc3ncc(C4CC4)cn3)cc2C)c2c1C(=O)NC2]

Synthetic Route:

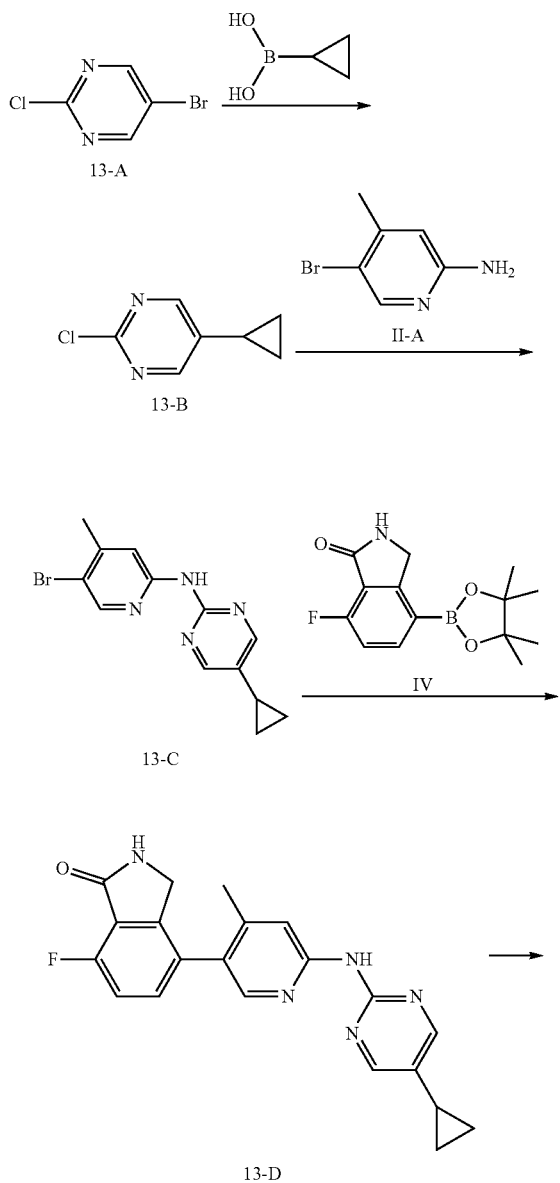

Step 1: Synthesis of Compound 13-B

13-A (1 g, 5.17 mmol) was dissolved in toluene (30 mL) and water (6 mL). Cyclopropylboronic acid (53.89 mg, 6.20 mmol), tricyclohexylphosphine (289.96 mg, 1.03 mmol), and potassium phosphate (3.29 g, 15.51 mmol) were added. The reaction solution was subjected to replacement with N2 three times, added with palladium acetate (116.07 mg, 516.99 μmol), and stirred at 100° C. for 12 hours under N2 protection. The reaction solution was filtered through celite, and the filtrate was subjected to rotary evaporation under reduced pressure. And then water (100 mL) was added, and the resulting reaction solution was extracted with ethyl acetate (100 mL), washed with saturated brine (100 mL), dried over sodium sulfate, filtered off the desiccant, and concentrated under reduced pressure to obtain a crude product. The crude product was purified by column chromatography (eluent, petroleum ether:ethyl acetate=10:1) to obtain compound 13-B.

MS m/z: 154.8[M+H]$^+$

Step 2: Synthesis of Compound 13-C

II-A (542.01 mg, 2.90 mmol) was dissolved in 1,4-dioxane (20 mL), and 13-B (560 mg, 3.62 mmol, 1 eq), BINAP (451.10 mg, 724.47 μmol, 0.2 eq), and cesium carbonate (3.54 g, 10.87 mmol, 3 eq) were added. The reaction solution was subjected to replacement with N2 three times, added with palladium acetate (81.32 mg, 362.23 μmol, 0.1 eq), and stirred at 100° C. for 1 hour under N2 protection. The resulting reaction solution was filtered with celite. The filtrate was added with H$_2$O (100 mL), extracted with DCM (100 mL), washed with saturated sodium chloride solution (100 mL), dried over sodium sulfate, filtered off the desiccant, and concentrated under reduced pressure to obtain a crude product. The crude product was purified by chromatography to obtain compound 13-C.

MS m/z: 304.8[M+H]$^+$

Step 3: Synthesis of Compound 13-D

Compound 13-D was prepared with the same method as compound 5 in example 5, except that the corresponding raw materials were used.

MS m/z: 376.0[M+H]$^+$

Step 4: Synthesis of Compound 13

Compound 13 was prepared with the same method as compound 10 in example 10, except that the corresponding raw materials were used.

MS m/z: 387.0[M+H]$^+$

1H NMR (400 MHz, DMSO-d6) δ ppm 12.18 (br s, 1H), 8.59 (s, 2H), 8.36 (s, 1H), 8.28 (s, 1H), 7.61 (s, 1H), 7.30 (d, J=8.3 Hz, 1H), 6.65 (d, J=8.3 Hz, 1H), 4.12 (s, 2 H), 2.89 (s, 3H), 2.30 (s, 3H), 2.04 (dt, J=4.3, 8.8 Hz, 1H), 1.09-1.03 (m, 2H), 0.89-0.84 (m, 2H).

Example 14: Compound 14

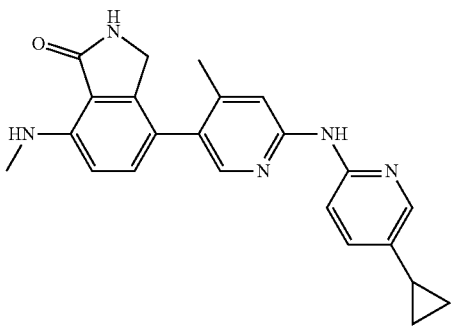 [SMILES: CNc1ccc(-c2cnc(Nc3ccc(C4CC4)cn3)cc2C)c2c1C(=O)NC2]

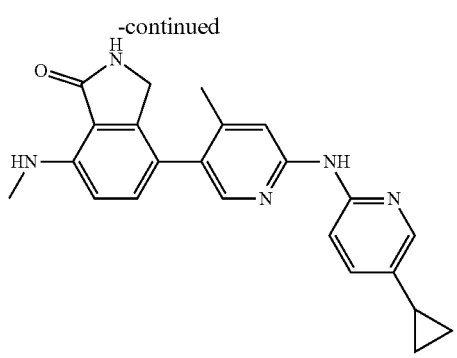

14

Synthetic Route:

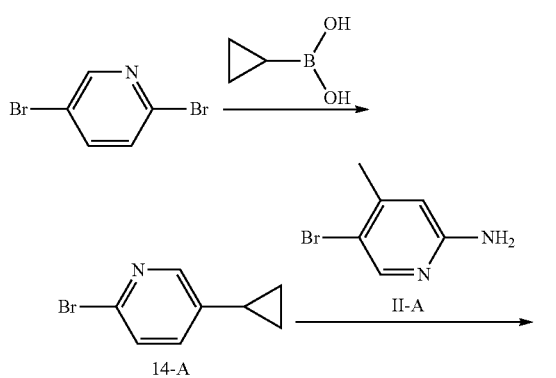

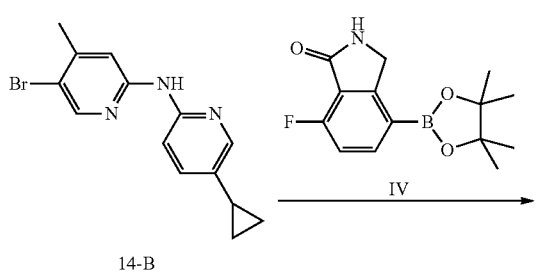

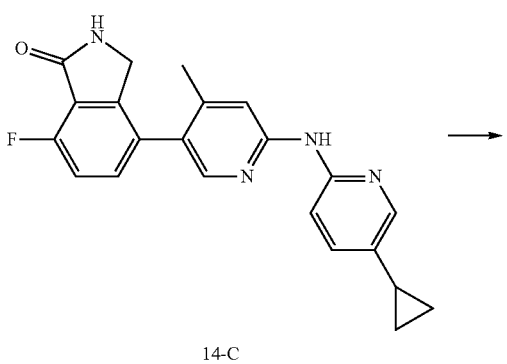

Step 1: Synthesis of Compound 14-A 2,5-dibromopyridine (15 g, 63.32 mmol) was dissolved in toluene (200 mL) and water (20 mL), and cyclopropylboronic acid (16.32 g, 189.96 mmol) and $K_3PO_4$ (40.32 g, 189.96 mmol) were added. The resulting reaction solution was subjected to replacement with $N_2$ three times, added with tricyclohexylphosphine (3.55 g, 12.66 mmol) and Pd(OAc)$_2$ (1.42 g, 6.33 mmol), and stirred at 100° C. for 4 hours under $N_2$ protection. The resulting reaction solution was added with $H_2O$ (400 mL), extracted with ethyl acetate (300 mL), separated, washed twice with $H_2O$ (400 mL), washed with saturated brine (250 mL), dried over anhydrous sodium sulfate, filtered off the desiccant, and concentrated under reduced pressure to obtain a concentrate. The concentrate was purified by column chromatography (eluent: petroleum ether:ethyl acetate=100:1 to 8:1) to obtain 14-A.

MS m/z: 197.8[M+H]$^+$

Step 2: Synthesis of Compound 14-B

Compound 14-B was prepared with the same method as compound 5-C in example 5, except that the corresponding raw materials were used.

MS m/z: 303.9[M+H]$^+$ $^1$H NMR (400 MHz, CHLOROFORM-d) δ ppm 8.25 (s, 1H), 8.10 (d, J=2.0 Hz, 1H), 7.50 (s, 1H), 7.35-7.28 (m, 2H), 7.15 (s, 1H), 2.38 (s, 3H), 1.91-1.81 (m, 1H), 1.00-0.92 (m, 2H), 0.70-0.62 (m, 2H)

Step 3: Synthesis of Compound 14-C

Compound 14-C was prepared with the same method as compound 5 in example 5, except that the corresponding raw materials were used.

MS m/z: 375.1[M+M]$^+$

Step 4: Synthesis of Compound 14

Compound 14 was prepared with the same method as compound 11 in example 11, except that the corresponding raw materials were used.

MS m/z: 386.1[M+H]$^+$

1H NMR (400 MHz, DMSO-d6) δ=12.86-12.71 (m, 1H), 8.34 (br s, 1H), 8.21 (d, J=2.0 Hz, 1H), 8.19 (s, 1H), 7.77 (dd, J=2.1, 8.9 Hz, 1H), 7.50-7.45 (m, 1H), 7.44 (br s, 1H), 7.28 (d, J=8.3 Hz, 1H), 6.65 (d, J=8.5 Hz, 1H), 4.11 (s, 2H), 2.89 (s, 3H), 2.24 (s, 3H), 2.08-2.01 (m, 1H), 1.06-0.99 (m, 2H), 0.77-0.72 (m, 2H)

Example 15: Compound 15

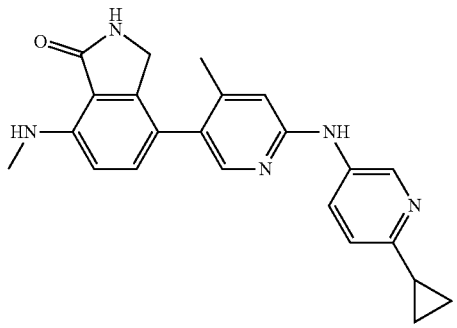 [SMILES: CNc1ccc(-c2cnc(Nc3ccc(C4CC4)nc3)cc2C)c2c1C(=O)NC2]

Synthetic Route:

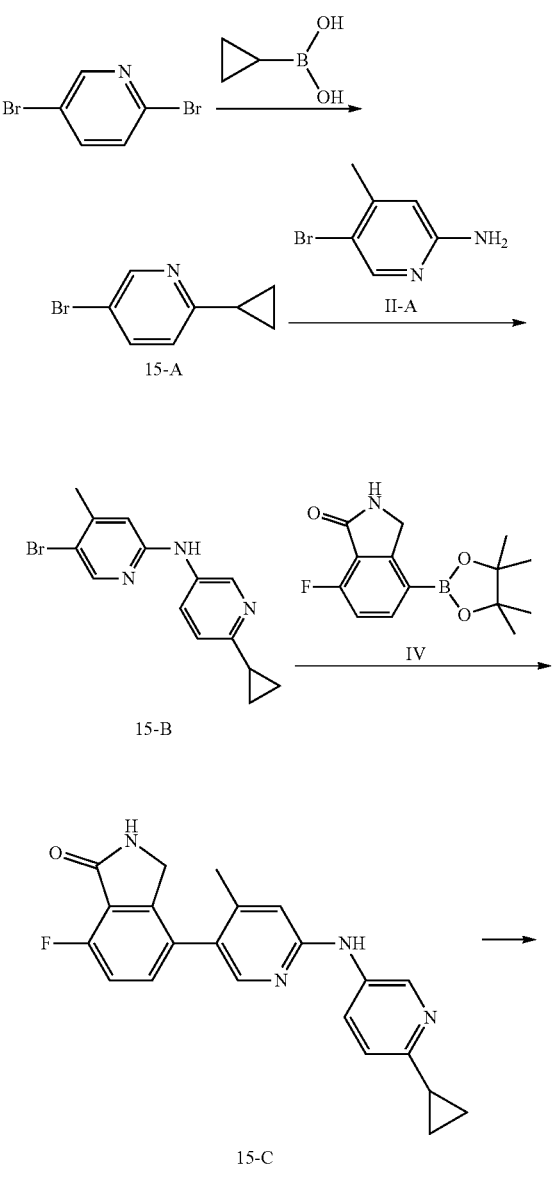

Step 1: Synthesis of Compound 15-A

Compound 15-A was prepared with the same method as compound 14-A in example 14, except that the corresponding raw materials were used.

MS m/z: 197.8[M+H]$^+$

Step 2: Synthesis of Compound 15-B

Compound 15-B was prepared with the same method as compound 5-C in example 5, except that the corresponding raw materials were used.

MS m/z: 303.9[M+H]$^+$

Step 3: Synthesis of Compound 15-C

Compound 15-C was prepared with the same method as compound 5 in example 5, except that the corresponding raw materials were used.

MS m/z: 375.1 [M+H]$^+$

Step 4: Synthesis of Compound 15

Compound 15 was prepared with the same method as compound 11 in example 11, except that the corresponding raw materials were used.

MS m/z: 386.1 [M+H]$^+$

1H NMR (400 MHz, DMSO-d6) δ ppm 10.79 (br s, 1H), 9.25 (br s, 1H), 8.47 (br d, J=8.0 Hz, 1H), 8.31 (br s, 1H), 8.08 (s, 1H), 7.59 (br d, J=9.0 Hz, 1H), 7.21 (br d, J=8.0 Hz, 1H), 7.06 (br s, 1H), 6.64 (br d, J=8.3 Hz, 1H), 4.10 (s, 2H), 2.87 (s, 3H), 2.49-2.42 (m, 1H), 2.12 (s, 3H), 1.28 (br d, J=5.8 Hz, 2H), 1.14 (br s, 2H)

Example 16: Compound 16

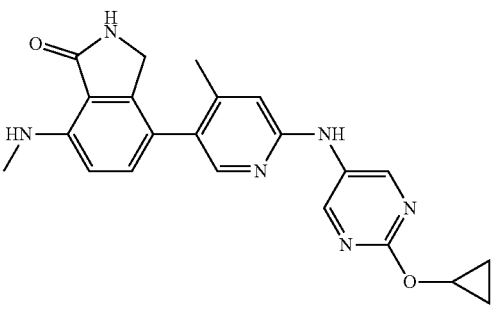 [SMILES: CNc1ccc(-c2cnc(Nc3cnc(OC4CC4)nc3)cc2C)c2c1C(=O)NC2]

Synthetic Route:

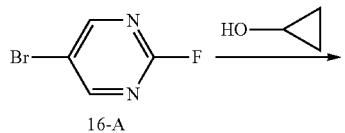

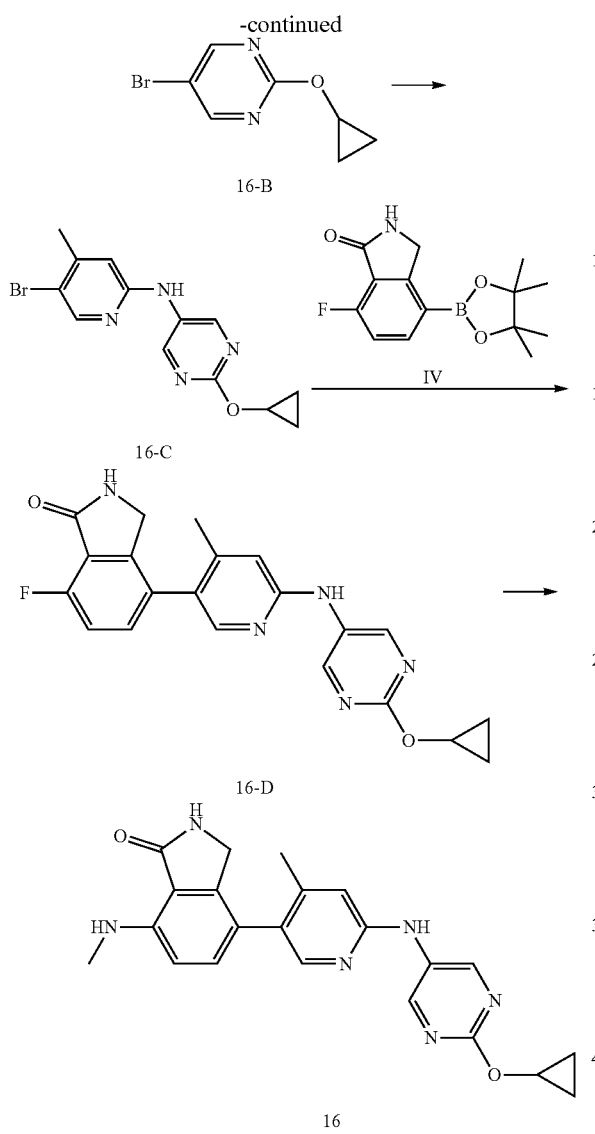

Step 1: Synthesis of Compound 16-B

Under nitrogen protection, sodium hydrogen (518.67 mg, 12.97 mmol, 60% purity) was added to tetrahydrofuran (20 mL), and cyclopropanol (376.58 mg, 6.48 mmol) was added thereto at 0° C., and the resulting reaction solution was stirred at 17° C. for 0.5 hour. 16-A (765 mg, 4.32 mmol) was added at 0° C., and the resulting reaction solution was stirred at 17° C. for 2 hours under nitrogen protection. The reaction solution was added dropwise with a saturated ammonium chloride solution (10 mL) at 0° C., extracted with ethyl acetate (40 mL), washed with saturated brine (30 mL), dried over anhydrous $Na_2SO_4$, filtered off the desiccant, and concentrated under reduced pressure to obtain a crude product. The crude product was purified by column chromatography (eluent PE:EA=80:1 to 10:1) to obtain compound 16-B.

MS m/z: 214.7[M+H]$^+$

Step 2: Synthesis of Compound 16-C

Compound 16-C was prepared with the same method as compound 5-C in example 5, except that the corresponding raw materials were used.

MS m/z: 320.7[M+H]$^+$

Step 3: Synthesis of Compound 16-D

Compound 16-D was prepared with the same method as compound 5 in example 5, except that the corresponding raw materials were used.

MS m/z: 392.0[M+H]$^+$

Step 4: Synthesis of Compound 16

Compound 16 was prepared with the same method as compound 11 in example 11, except that the corresponding raw materials were used.

MS m/z: 403.1 [M+H]$^+$

1H NMR (400 MHz, METHANOL-d4) δ ppm 8.72 (s, 2H), 7.81 (s, 1H), 7.38 (d, J=8.3 Hz, 1H), 7.21 (s, 1H), 6.93 (d, J=8.3 Hz, 1H), 4.43 (tt, J=3.2, 6.1 Hz, 1H), 4.24 (s, 2H), 3.02 (s, 3H), 2.28 (s, 3H), 0.89-0.81 (m, 4H)

Example 17: Compound 17

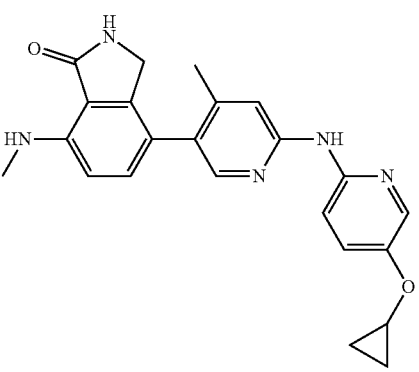 [SMILES: CNc1ccc(-c2cnc(Nc3ccc(OC4CC4)cn3)cc2C)c2c1C(=O)NC2]

Synthetic Route:

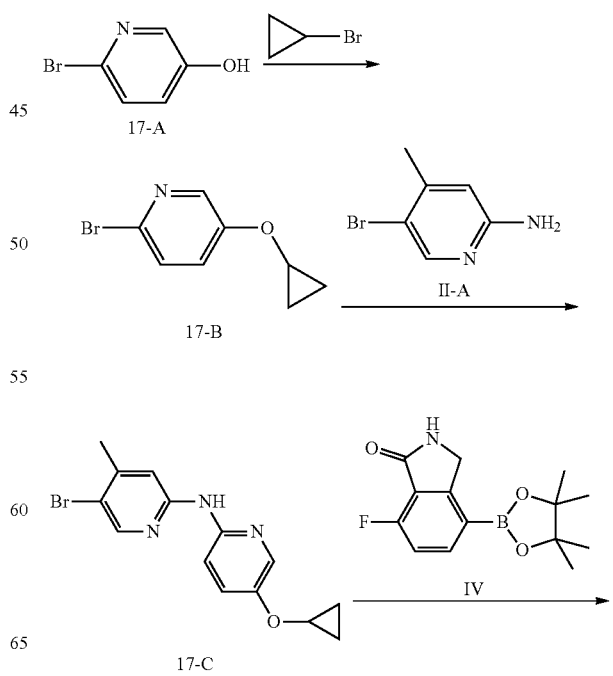

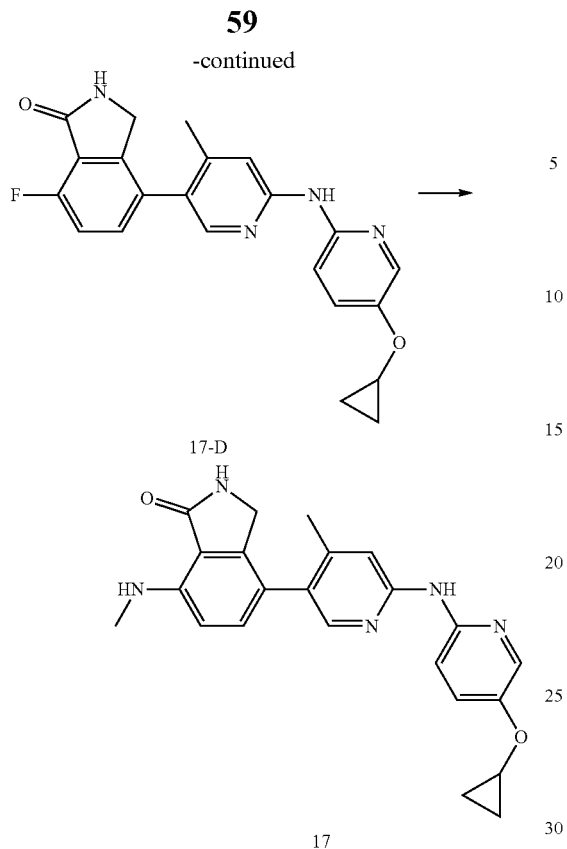

17-D

17

Step 1: Synthesis of Compound 17-B

17-A (2 g, 11.49 mmol) was dissolved in N,N-dimethylformamide (50 mL), and cyclopropyl bromide (4.17 g, 34.48 mmol), cesium carbonate (11.24 g, 34.48 mmol), and potassium iodide (1.91 g, 11.49 mmol) were added. The resulting reaction solution was stirred at 140° C. for 20 hours under nitrogen protection. Then the reaction solution was added with water (500 mL), extracted with ethyl acetate (500 mL), washed with water (200 mL), washed with saturated brine (200 mL), dried over sodium sulfate, filtered off the desiccant, and concentrated under reduced pressure to obtain a crude product. The crude product was purified by preparative column chromatography (eluent, petroleum ether:ethyl acetate=10:1) to obtain compound 17-B.

MS m/z: 213.8[M+H]

Step 2: Synthesis of Compound 17-C

Compound 17-C was prepared with the same method as compound 5-C in example 5, except that the corresponding raw materials were used.

MS m/z: 319.9[M+H]

$^1$H NMR (400 MHz, CHLOROFORM-d) δ ppm 8.23 (s, 1H) 8.10 (d, J=2.76 Hz, 1H) 7.38-7.44 (m, 2H) 7.31-7.37 (m, 1H) 7.10-7.21 (m, 1H) 3.72-3.80 (m, 1H) 2.37 (s, 3H) 0.79 (d, J=4.52 Hz, 4H)

Step 3: Synthesis of Compound 17-D

Compound 17-D was prepared with the same method as compound 5 in example 5, except that the corresponding raw materials were used.

MS m/z: 391.0[M+H]

Step 4: Synthesis of Compound 17

Compound 17 was prepared with the same method as compound 11 in example 11, except that the corresponding raw materials were used.

MS m/z: 402.1[M+H]$^+$

1H NMR (400 MHz, METHANOL-d$_4$) δ ppm 8.27 (d, J=2.8 Hz, 1H), 8.13 (s, 1H), 7.77 (dd, J=2.8, 9.3 Hz, 1H), 7.41 (d, J=8.3 Hz, 1H), 7.27 (s, 1H), 7.25 (d, J=9.3 Hz, 1H), 6.94 (d, J=8.3 Hz, 1H), 4.26 (s, 2H), 3.96 (td, J=3.0, 5.7 Hz, 1H), 3.04 (s, 3H), 2.34 (s, 3H), 0.93-0.86 (m, 2H), 0.82-0.77 (m, 2H)

Example 18: Compound 18

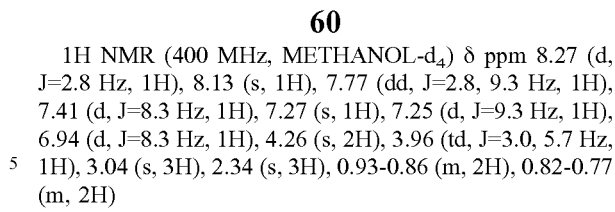

Synthetic Route:

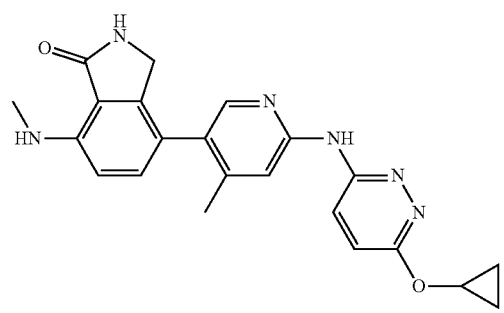 [SMILES: CNc1ccc(-c2cnc(Nc3ccc(OC4CC4)nn3)cc2C)c2c1C(=O)NC2]

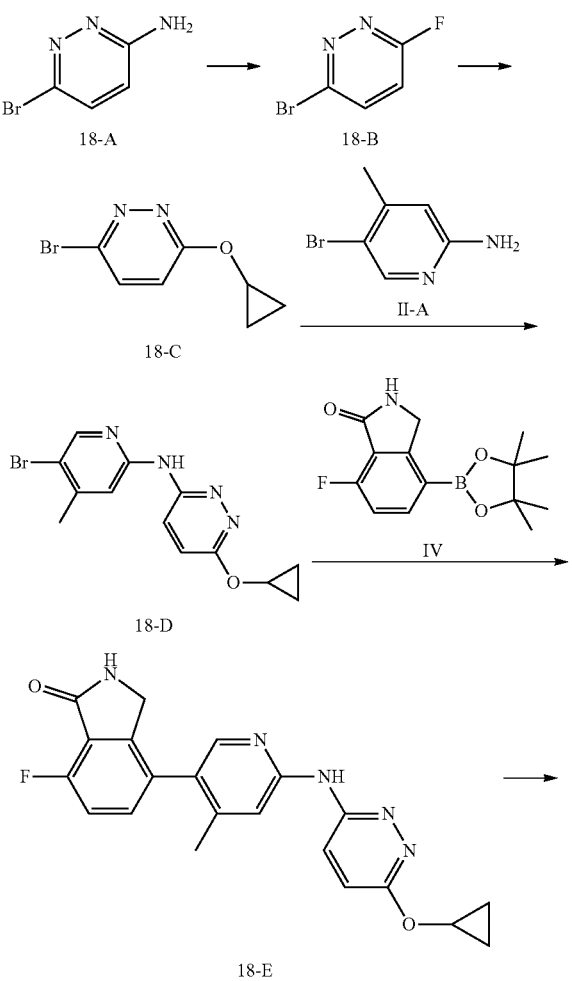

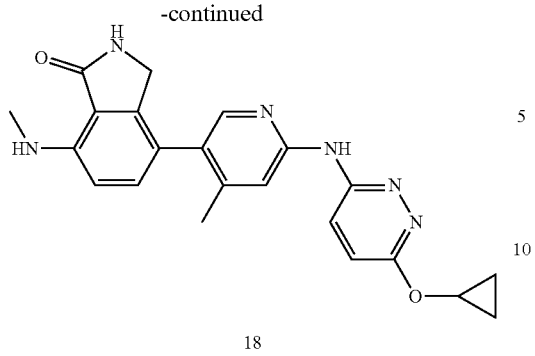

18

Step 1: Synthesis of Compound 18-B

18-A (200 mg, 1.15 mmol) was dissolved in a pyridine hydrofluoride solution (5 mL), and sodium nitrite (79.31 mg, 1.15 mmol) was added slowly at 0° C. The resulting reaction solution was stirred at 0° C. for 1.5 hours. Then the reaction solution was adjusted to pH=8 with a saturated sodium bicarbonate solution, washed with water (300 mL), extracted with ethyl acetate (150 mL), and separated. The organic phase was washed with saturated brine (50 mL), dried over anhydrous $Na_2SO_4$, and concentrated under reduced pressure to obtain a concentrate. The concentrate was purified by column chromatography (eluent: PE:EA=10:1 to 8:1), and subjected to rotary evaporation under reduced pressure to obtain compound 18-B.

MS m/z: 176.8[M+H]$^+$.

$^1$HNMR (400 MHz, CHLOROFORM-d) δ ppm 7.77 (dd, J=6.5, 9.0 Hz, 1H), 7.14 (dd, J=2.0, 9.0 Hz, 1H)

Step 2: Synthesis of Compound 18-C

Sodium hydrogen (113.00 mg, 2.83 mmol) was added to a three-necked flask, and THF (5 mL) was added, and cyclopropanol (24.61 mg, 423.79 μmol) dissolved in THF (1 mL) was added dropwise at 0° C. and stirred at 0° C. for 0.5 hour. 18-B (50 mg, 245.80 μmol) was added, and the resulting reaction solution was stirred at 30° C. for 1 hour under nitrogen protection. And then an ammonium chloride solution was added at 0° C. until no bubbles emerge. The crude product was washed with $H_2O$ (150 mL), extracted with EA (50 mL), washed with saturated brine (50 mL), dried over anhydrous $Na_2SO_4$, filtered off the desiccant, and concentrated under reduced pressure to obtain a concentrate. The concentrate was purified by column chromatography (eluent: PE:EA=20:1 to 5:1), and concentrated under reduced pressure to obtain 18-C.

MS m/z: 214.8[M+H]$^+$.

$^1$H NMR (400 MHz, CHLOROFORM-d) δ ppm 7.49 (d, J=9.0 Hz, 1H), 6.83 (d, J=9.0 Hz, 1H), 4.47 (tt, J=3.0, 6.2 Hz, 1H), 0.92-0.85 (m, 2H), 0.85-0.78 (m, 2H)

Step 3: Synthesis of Compound 18-D

Compound 18-D was prepared with the same method as compound 5-C in example 5, except that the corresponding raw materials were used.

MS m/z: 320.8[M+H]$^+$

Step 4: Synthesis of Compound 18-E

Compound 18-E was prepared with the same method as compound 5 in example 5, except that the corresponding raw materials were used.

MS m/z: 392.0[M+H]$^+$

Step 5: Synthesis of Compound 18

Compound 18 was prepared with the same method as compound 11 in example 11, except that the corresponding raw materials were used.

MS m/z: 403.0[M+H]$^+$ $^1$H NMR (400 MHz, DMSO-d6) δ ppm 8.36 (br s, 1H), 8.29 (s, 1H), 7.88 (d, J=9.3 Hz, 1H), 7.59-7.51 (m, 2H), 7.31 (d, J=8.3 Hz, 1H), 6.66 (d, J=8.3 Hz, 1H), 4.44-4.18 (m, 1H), 4.12 (s, 2H), 2.89 (s, 3H), 2.30 (s, 3H), 0.89-0.83 (m, 2H), 0.82-0.78 (m, 2H)

Example 19: Compound 19

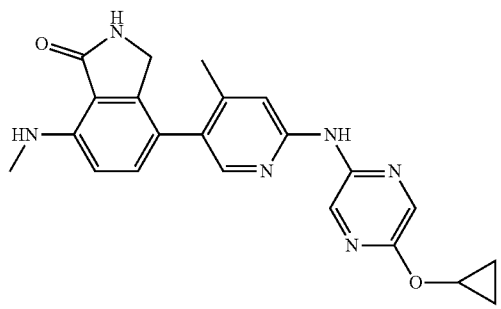 [SMILES: CNc1ccc(-c2cnc(Nc3cnc(OC4CC4)cn3)cc2C)c2c1C(=O)NC2]

Synthetic Route:

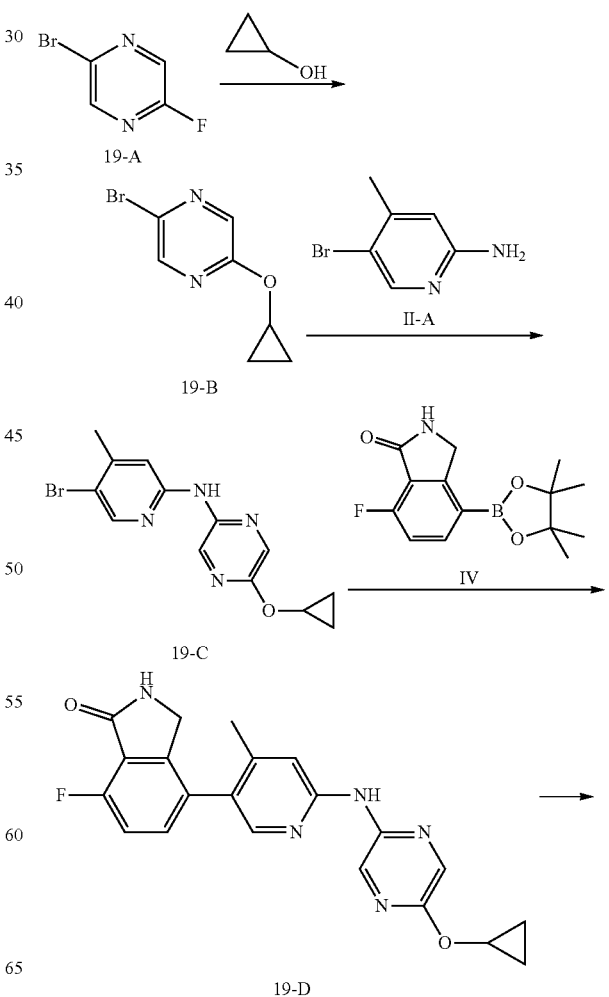

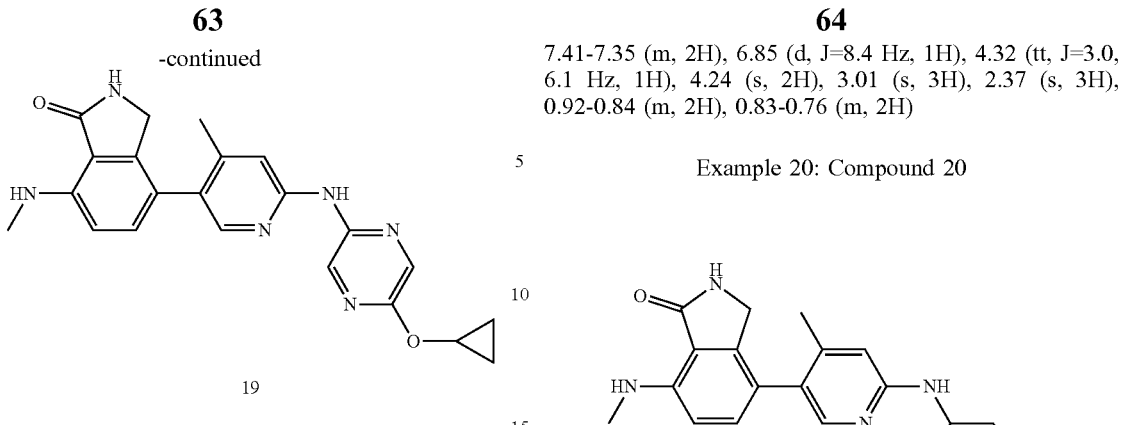

19

Step 1: Synthesis of Compound 19-B

NaH (33.90 mg, 847.58 mol, 60% purity) was added to tetrahydrofuran (5 mL), and cyclopropanol (24.61 mg, 423.79 μmol) was added at 0° C. After the resulting reaction solution was stirred at 25° C. for 30 minutes, the temperature was reduced to 0° C. and 19-A (50 mg, 282.53 μmol) was added. The resulting reaction solution was stirred at 25° C. for 1.5 hour, and then a saturated ammonium chloride solution (5 mL) was added dropwise at 0° C. to quench the reaction. The resulting reaction solution was extracted with ethyl acetate (30 mL), washed with brine (20 mL), dried over sodium sulfate, filtered off the desiccant, and concentrated under reduced pressure to obtain a crude product. The crude product was purified by preparative TLC (developing agent: petroleum ether/ethyl acetate=10/1) to obtain 19-B.

MS m/z: 214.5[M+H]+

$^1$H NMR (400 MHz, CDCl$_3$) δ ppm 8.27 (s, 1H) 8.03 (s, 1H) 4.25 (tt, J=6.05, 3.11 Hz, 1H) 0.78-0.91 (m, 4H)

Step 2: Synthesis of Compound 19-C

19-B (50 mg, 232.51 μmol) was dissolved in dioxane (10 mL), and 2-amino-4-methyl-5-bromopyridine (39.14 mg, 209.26 μmol), 4,5-bisdiphenylphosphine-9,9-dimethylxanthene (53.81 mg, 93.00 μmol), and cesium carbonate (227.27 mg, 697.52 μmol) were added. The resulting reaction solution was subjected to replacement with N$_2$ three times, and then added with palladium acetate (10.44 mg, 46.50 μmol), and stirred at 90° C. for 12 hours under N$_2$ protection. And then the resulting reaction solution was filtered through celite. The filtrate was added with water (50 mL), extracted with ethyl acetate (80 mL), washed with saturated brine (50 mL), dried over sodium sulfate, filtered off the desiccant, and concentrated under reduced pressure to obtain a crude product. The crude product was purified by preparative TLC (developing agent, petroleum ether:ethyl acetate=3:1) to obtain compound 19-C.

MS m/z: 320.7[M+H]$^+$ $^1$H NMR (400 MHz, CDCl$_3$) δ ppm 8.55 (d, J=1.25 Hz, 1H) 8.19 (s, 1H) 7.85 (d, J=1.51 Hz, 1H) 7.15 (s, 1H) 4.05-4.16 (m, 1H) 2.30 (s, 3H) 0.70-0.78 (m, 4H)

Step 3: Synthesis of Compound 19-D

Compound 19-D was prepared with the same method as compound 5 in example 5, except that the corresponding raw materials were used.

MS m/z: 392.0[M+H]$^+$

Step 4: Synthesis of Compound 19

Compound 19 was prepared with the same method as compound 11 in example 11, except that the corresponding raw materials were used.

MS m/z: 403.1 [M+H]$^+$ $^1$H NMR (400 MHz, METHANOL-d$_4$) δ ppm 8.26 (d, J=1.4 Hz, 1H), 8.15 (d, J=1.4 Hz, 1H), 8.09 (s, 1H), 7.41-7.35 (m, 2H), 6.85 (d, J=8.4 Hz, 1H), 4.32 (tt, J=3.0, 6.1 Hz, 1H), 4.24 (s, 2H), 3.01 (s, 3H), 2.37 (s, 3H), 0.92-0.84 (m, 2H), 0.83-0.76 (m, 2H)

Example 20: Compound 20

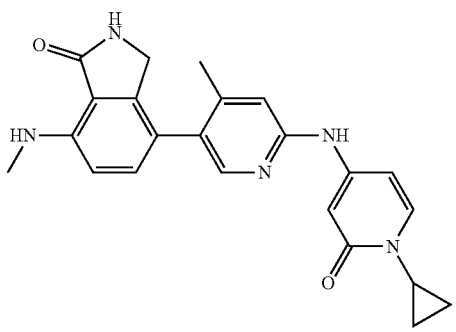 [SMILES: CNc1ccc(-c2cnc(Nc3ccn(C4CC4)c(=O)c3)cc2C)c2c1C(=O)NC2]

Synthetic Route:

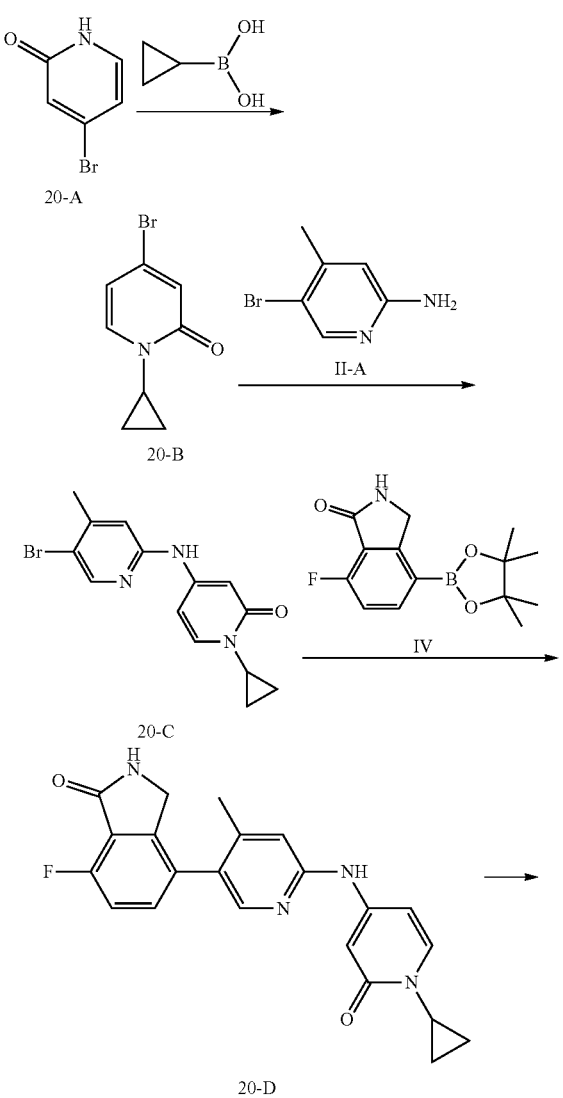

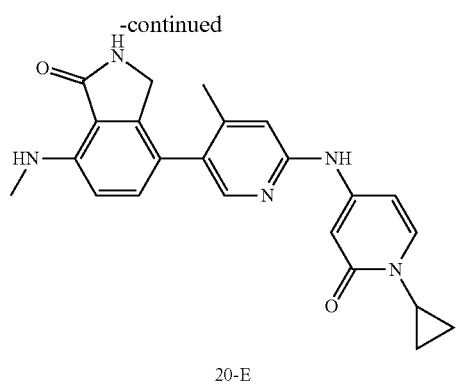

20-E

Step 1: Synthesis of Compound 20-B

Compound 20-A (2 g, 11.49 mmol) and cyclopropylboronic acid (1.97 g, 22.99 mmol) were dissolved in 1,2-dichloroethane (30 mL), and copper acetate (2.09 g, 11.49 mmol), pyridine (909.22 mg, 11.49 mmol, 927.78 μL) and sodium carbonate (3.05 g, 28.74 mmol) were added. After the reaction system was stirred at 70° C. for 12 hours, the mixed system was filtered through celite, and the filtrate was collected, and concentrated to obtain a crude product, which was separated and purified by chromatography column (SiO$_2$, petroleum ether/ethyl acetate=1:0 to 1:1) to obtain compound 20-B.

MS m/z: 213.8[M+H]+

Step 2: Synthesis of Compound 20-C

Compound 20-B (500 mg, 2.34 mmol) and 5-bromo-4-methyl-pyridine-2-pyridine (655.32 mg, 3.50 mmol) were dissolved in toluene (20 mL), and Xantphos (270.31 mg, 467.16 μmol) and cesium carbonate (2.28 g, 7.01 mmol) were added. Palladium acetate (78.66 mg, 350.37 μmol) was added under a nitrogen atmosphere, and then the resulting system was stirred under a nitrogen atmosphere at 90° C. for 5 hours, and concentrated to obtain a crude product. The crude product was separated and purified by chromatography column (SiO$_2$, dichloromethane/tetrahydrofuran=1:1 to dichloromethane/methanol=10:1) to obtain compound 20-C.

MS m/z: 319.9[M+H]$^+$

Step 3: Synthesis of Compound 20-D

Compound 20-D was prepared with the same method as compound 5 in example 5, except that the corresponding raw materials were used.

MS m/z: 391.1[M+H]$^+$

Step 4: Synthesis of Compound 20

Compound 20 was prepared with the same method as compound 11 in example 11, except that the corresponding raw materials were used.

MS m/z: 402.1[M+H]$^+$

1H NMR (400 MHz, METHANOL-d$_4$) δ ppm 8.19 (s, 1H), 7.95 (d, J=7.5 Hz, 1H), 7.87 (s, 1H), 7.33 (d, J=8.3 Hz, 1H), 7.12 (s, 1H), 7.03 (br d, J=7.5 Hz, 1H), 6.86 (d, J=8.3 Hz, 1H), 4.19 (s, 2H), 3.58-3.50 (m, 1H), 3.02 (s, 3H), 2.25 (s, 3H), 1.27-1.20 (m, 2H), 1.16-1.07 (m, 2H).

Experimental Example 1: In Vitro Inhibitory Activity of the Compounds of the Present Invention on CSF-1R in Terms of Enzymology The compounds of the present invention for experiments were made in house, and their structural formulas were shown in the preparation examples of each compound. The experimental tests were conducted at Reaction Biology Corporation in the United States, and the experimental results were provided by the company.

Experimental Reagents:

Necessary reaction buffer: 20 mM hydroxyethylpiperazine ethanesulfonic acid (pH 7.5), 10 mM magnesium chloride, 1 mM EGTA, 0.02% Brij35, 0.02 mg/mL bovine serum albumin, 0.1 mM Na$_3$VO$_4$, 2 mM DTT, 1% DMSO.

The necessary cofactors were added separately to the CSF-1R kinase reaction.

Enzyme: the concentration of CSF-1R was 2.5 nM

Treatment with the Compounds:

The compound to be tested was formulated with 100% DMSO into a solution with a specific concentration, and serial dilution was performed with DMSO through the intelligent pipetting assistant Integra Viaflo Assist.

Experimental Procedure:

Preparation of fresh necessary reaction buffer;

All necessary cofactors were added to the above reaction buffer;

CSF-1R kinase was added to the above matrix solution and shaken gently;

Using acoustic technology (Echo550; nanoliter range), a solution of the compound in DMSO was added to the above kinase reaction mixture, and the reaction solution was incubated at room temperature for 20 minutes;

$^{33}$P-ATP (specific activity, 10 μCi/μl) was added to the above kinase reaction mixture to initiate the reaction;

The reaction solution was incubated at room temperature for 2 hours;

The kinase activity was detected by the filter-binding method;

The kinase activity was the ratio of the remaining kinase in the test sample to the vehicle (DMSO) group. IC$_{50}$ values and profiles were obtained using Prism (GraphPad software). The measurement results were shown in Table 1.

TABLE 1

In vitro activity determination results of the compounds of the present invention (IC$_{50}$) in terms of enzymology

| Compound No. | CSF-1R (IC$_{50}$ nM) |
|---|---|
| 1 | 3.06 |
| 2 | 1.55 |
| 3 | 24.5 |
| 4 | 1.27 |
| 5 | 1.68 |
| 6 | 5.01 |
| 7 | 1.87 |
| 8 | 4.98 |
| 9 | 1.41 |
| 10 | 2.61 |
| 11 | 4.71 |
| 12 | 1.89 |
| 13 | 3.78 |
| 14 | 2.50 |
| 15 | 0.82 |
| 16 | 2.49 |
| 17 | 4.15 |
| 18 | 3.43 |
| 19 | 2.55 |
| 20 | 12.10 |

Experimental conclusions: The compounds of the present invention had a significant inhibitory effect on CSF-1R kinase.

Example 2 Pharmacokinetic Study on Mice and Rats (PK)

Experimental Purpose:

The purpose of this experiment was to study the pharmacokinetics of the test article in the plasma of male C57BL/6J mice and SD rats after intravenous injection and oral administration.

Experimental Method:

The animals were randomly divided into two groups with 2 males in each group. The compounds were formulated into prescribed preparations. Preparations for intravenous injection were clear solutions, and oral preparations could be clear or homogeneous suspensions.

Whole blood samples were collected from the jugular vein puncture or saphenous vein of the animals 5 minutes, 15 minutes, 30 minutes, 1 hour, 2 hours, 4 hours, 6 hours, and 8 hours after administration. The whole blood sample was added to the centrifuge tube containing anticoagulant, and centrifuged at 3000 g for 15 minutes at 4° C. The supernatant of plasma was taken, frozen quickly on dry ice, and then stored in a −70° C.±10° C. refrigerator until LC-MS/MS analysis.

Data Processing:

WinNonlin™ Version 6.3.0 (Pharsight, Mountain View, Calif.) pharmacokinetic software was used to process the plasma drug concentration data of the compounds with a non-compartmental model. The peak concentration ($C_{max}$), peak time ($T_{max}$) and quantifiable end time were obtained directly from the blood drug concentration-time profile.

The following pharmacokinetic parameters were calculated using the log-linear trapezoid method: Plasma clearance rate (CL), volume of distribution (Vd), elimination phase half-life ($T_{1/2}$), average residence time of drug in the body from 0 to the end time point ($MRT_{0-last}$), average residence time of the drug in the body from 0 to infinite time ($MRT_{0-inf}$), area under the time-plasma concentration curve from 0 to the end time point ($AUC_{0-last}$), area under the time-plasma concentration curve from 0 to infinite time ($AUC_{0-inf}$) and bioavailability (F), $C_0$ was the initial concentration.

Experimental Results:

|  |  |  | Compound 10 | Control compound |
|---|---|---|---|---|
| PK | IV (1 mpk) | $C_0$ (nM) | 6292 | 3721 |
|  |  | $T_{1/2}$ (h): | 2.53 | 0.92 |
|  |  | Cl (mL/Kg/min) | 2.31 | 46.7 |
|  |  | Vd (L/kg) | 0.495 | 1.48 |
|  |  | $AUC_{0-last}$(nM · h) | 18739 | 918 |
|  | PO (10 mpk) | Cmax (nM) | 33050 | 104 |
|  |  | $AUC_{0-last}$(nM · h) | 198215 | 333 |
|  |  | F (%) | 106 | 3.92 |

Conclusion: The compounds of the present invention could significantly increase the pharmacokinetic drug concentration exposure, half-life and bioavailability of rats.

What is claimed is:

1. A compound represented by formula (I), a tautomer or stereoisomer thereof or a pharmaceutically acceptable salt thereof,

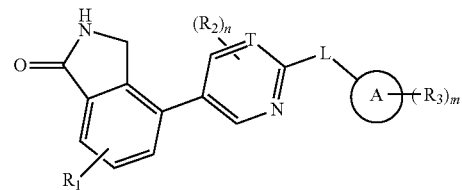

wherein

T is selected from —N— and —CH—;

$R_1$ is selected from —N($R_4$)($R_5$);

$R_2$ is independently selected from H, F, Cl, Br, I, OH, $NH_2$ and CN, or is independently selected from $C_{1-3}$ alkyl optionally substituted with 1, 2 or 3R;

$R_3$ is independently selected from H, F, C, Br, I, OH, $NH_2$, CN, $C_{1-6}$ alkyl, $C_{1-6}$ heteroalkyl, $C_{3-7}$ cycloalkyl and $C_{3-7}$ cycloalkyl-O—, and the $C_{1-6}$ alkyl, $C_{1-6}$ heteroalkyl, $C_{3-7}$ cycloalkyl and $C_{3-7}$ cycloalkyl-O— are optionally substituted with 1, 2 or 3R;

$R_4$ and $R_5$ are each independently selected from H, $C_{1-3}$ alkyl and $C_{1-3}$ alkyl-C(=O)—, and the $C_{1-3}$ alkyl and $C_{1-3}$ alkyl-C(=O)— are optionally substituted with 1, 2 or 3 substituents independently selected from F, Cl, Br, I, $NH_2$ and OH;

L is selected from —NH— and —NHCH$_2$—;

ring A is selected from phenyl, 5-6 membered heteroaryl and 6 membered heterocycloalkenyl;

n is selected from 0, 1 and 2;

m is selected from 1, 2 and 3;

each R is independently selected from H, F, Cl, Br, I, OH, $NH_2$, CN, $C_{1-6}$ alkyl and $C_{1-6}$ heteroalkyl, and the $C_{1-6}$ alkyl and $C_{1-6}$ heteroalkyl are optionally substituted with 1, 2 or 3 R';

R' is selected from F, Cl, Br, I, OH, $NH_2$, CN and Me;

the $C_{1-6}$ heteroalkyl, 5-6 membered heteroaryl and 6 membered heterocycloalkenyl independently contain 1, 2, 3 or 4 heteroatoms or heteroatomic groups independently selected from —O—, —S—, N or —NH—.

2. The compound, tautomer or stereoisomer thereof or pharmaceutically acceptable salt thereof according to claim 1, wherein R is selected from H, F, Cl, Br, I, OH, $NH_2$, CN, $C_{1-3}$ alkyl and $C_{1-3}$ alkoxy, and the $C_{1-3}$ alkyl and $C_{1-3}$ alkoxy, are optionally substituted with 1, 2 or 3 R'.

3. The compound, tautomer or stereoisomer thereof or pharmaceutically acceptable salt thereof according to claim 2, wherein R is selected from H, F, Cl, Br, I, OH, $NH_2$, CN, Me, Et,

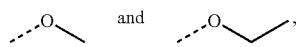

and the Me, Et,

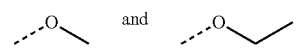

are optionally substituted with 1, 2 or 3 R'.

4. The compound, tautomer or stereoisomer thereof or pharmaceutically acceptable salt thereof according to claim 3, wherein R is selected from H, F, Cl, Br, I, OH, $NH_2$, CN, Me, $CH_2F$, $CHF_2$, $CF_3$, Et,

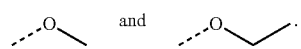

5. The compound, tautomer or stereoisomer thereof or pharmaceutically acceptable salt thereof according to claim 1, wherein R₂ is independently selected from H, F, Cl, Br, I, OH, NH₂, CN, Me and Et, and the Me and Et are optionally substituted with 1, 2 or 3R;

and/or, R₃ is independently selected from H, F, Cl, Br, I, OH, NH₂, CN, C₁₋₃ alkyl, C₁₋₃ alkoxy, C₁₋₃ alkylamino, cyclopropanyl and cyclopropanyl-O—, and the C₁₋₃ alkyl, C₁₋₃ alkoxy, C₁₋₃ alkylamino, cyclopropanyl and cyclopropanyl-O— are optionally substituted with 1, 2 or 3R;

and/or, R₄ and R₅ are independently selected from H, Me, Et and

and/or, ring A is selected from phenyl, pyridazinyl, pyrazinyl, pyrimidinyl, pyridin-2(1H)one and pyridyl.

6. The compound, tautomer or stereoisomer thereof or pharmaceutically acceptable salt thereof according to claim 5, wherein R₂ is selected from Me.

7. The compound, tautomer or stereoisomer thereof or pharmaceutically acceptable salt thereof according to claim 5, wherein R₃ is independently selected from H, F, Cl, Br, I, OH, NH₂, CN, Me,

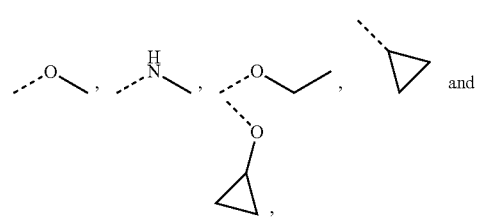

and the Me,

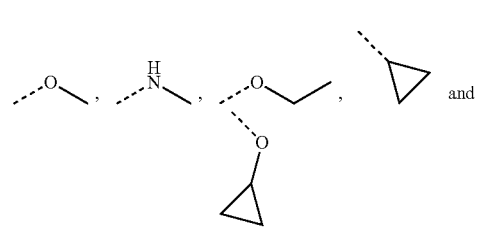

are optionally substituted with 1, 2 or 3R.

8. The compound, tautomer or stereoisomer thereof or pharmaceutically acceptable salt thereof according to claim 7, wherein R₃ is independently selected from H, F, Cl, Br, I, OH, NH₂, CN, Me,

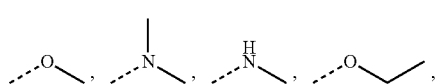

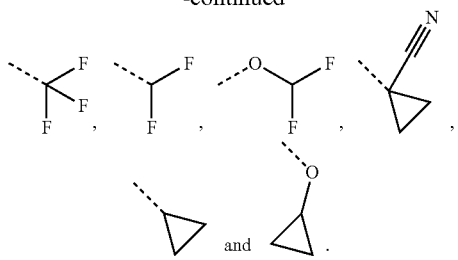

9. The compound, tautomer or stereoisomer thereof or pharmaceutically acceptable salt thereof according to claim 5, wherein R₁ is selected from NH₂,

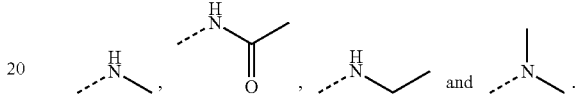

10. The compound, tautomer or stereoisomer thereof or pharmaceutically acceptable salt thereof according to claim 5, wherein structural unit

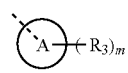

is selected from

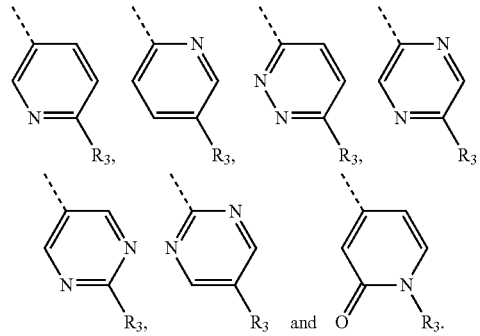

11. The compound, tautomer or stereoisomer thereof or pharmaceutically acceptable salt thereof according to claim 1, wherein structural unit

is selected from

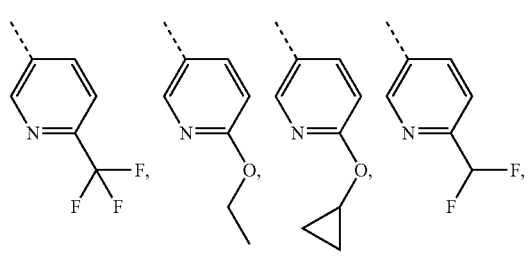

-continued
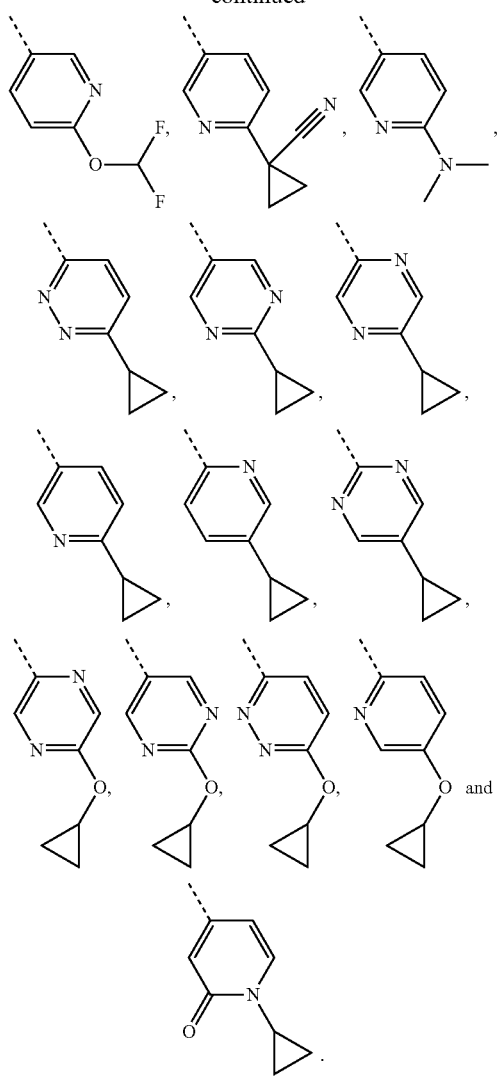
12. The compound, tautomer or stereoisomer thereof or pharmaceutically acceptable salt thereof according to claim 1, wherein structural unit
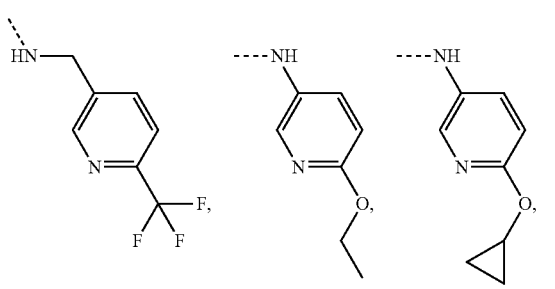
is selected from
-continued
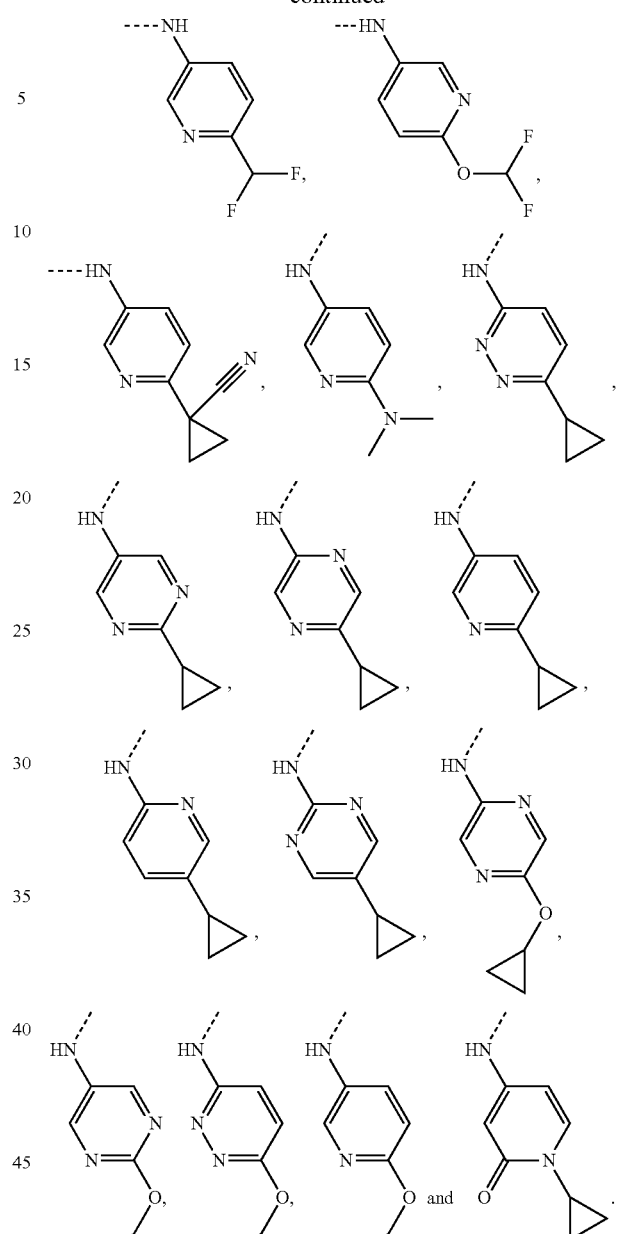
13. The compound, tautomer or stereoisomer thereof or pharmaceutically acceptable salt thereof according to claim 1, wherein structural unit
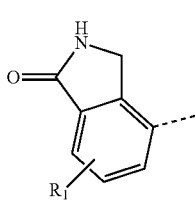

is selected from

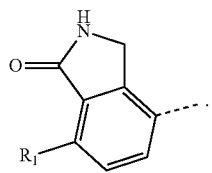

14. The compound, tautomer or stereoisomer thereof or pharmaceutically acceptable salt thereof according to claim 1, wherein structural unit

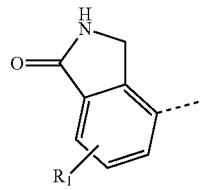

is selected from

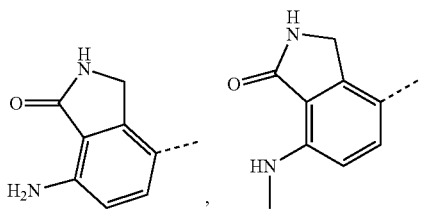

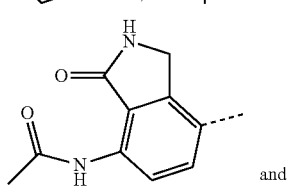

15. The compound, tautomer or stereoisomer thereof or pharmaceutically acceptable salt thereof according to claim 1, wherein structural unit

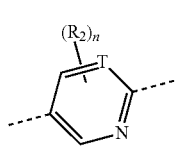

is selected from

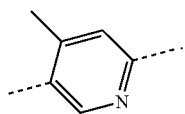

16. The compound, tautomer or stereoisomer thereof or pharmaceutically acceptable salt thereof according to claim 1, wherein the compound is selected from (I-1)

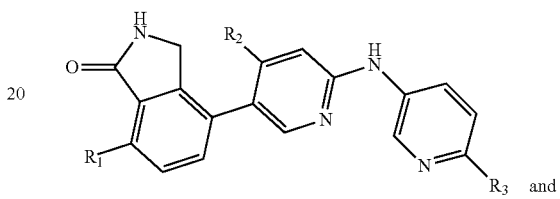 and (I-2)

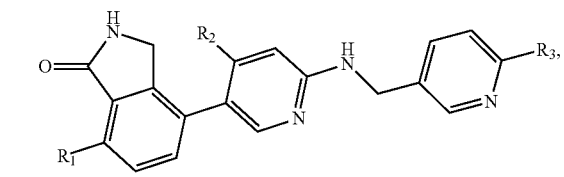, wherein $R_1$, $R_2$ and $R_3$ are as defined in claim 1.

17. A compound, a tautomer or stereoisomer thereof or a pharmaceutically acceptable salt thereof, wherein the compound is selected from:

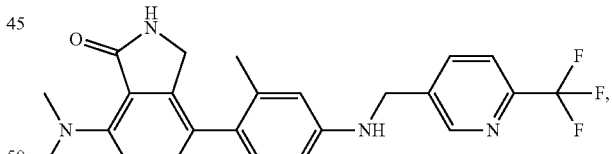

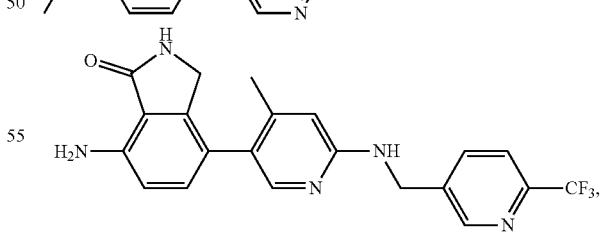

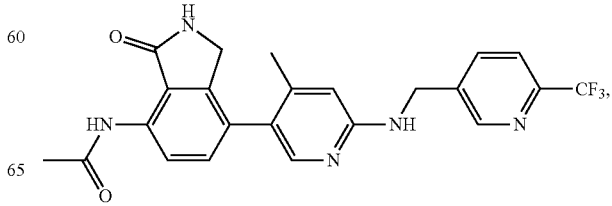

75
-continued
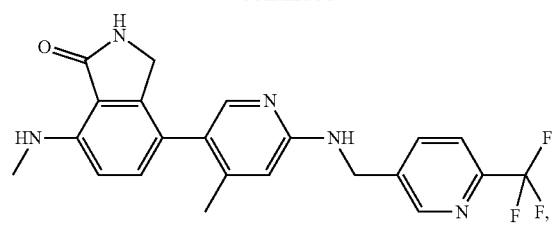
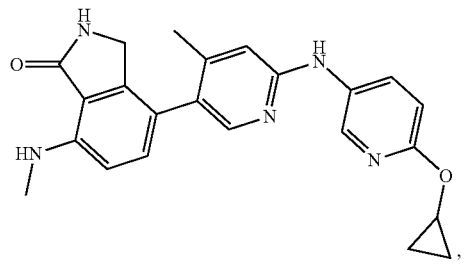
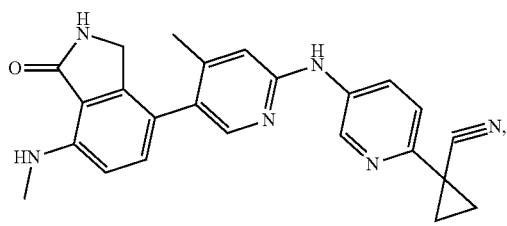
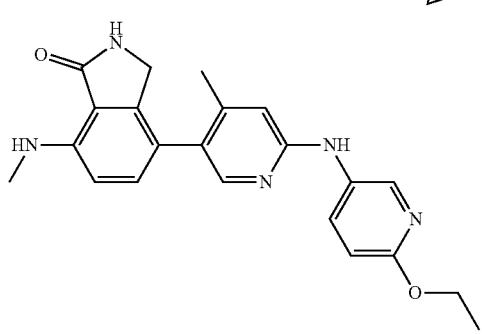
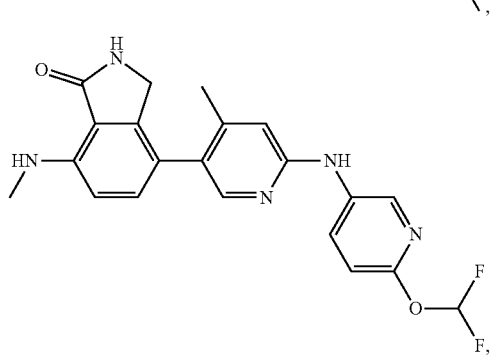
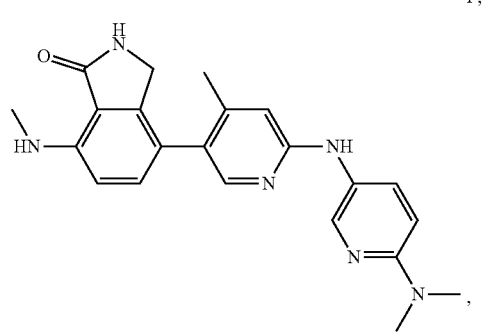
76
-continued
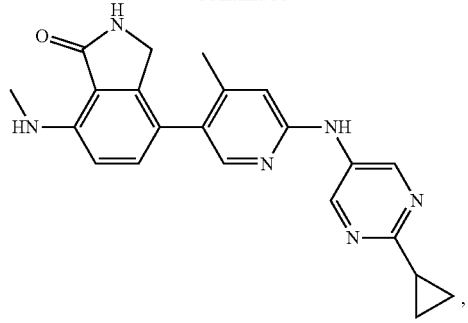
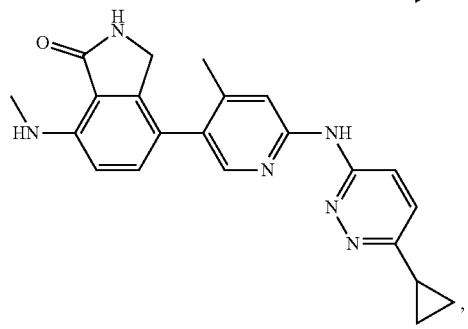
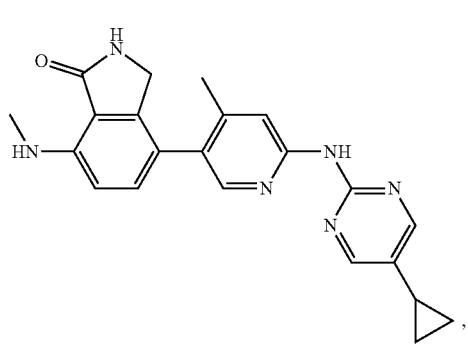

-continued

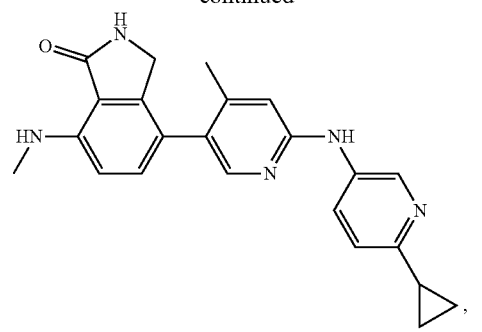

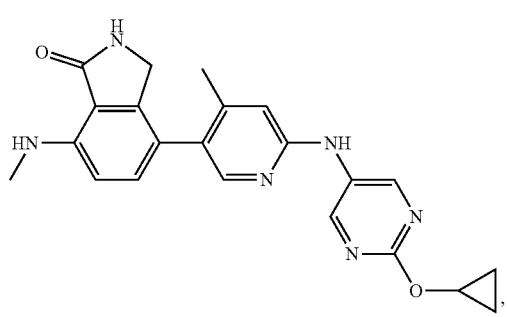

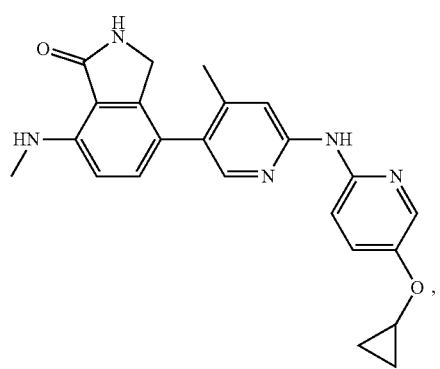

-continued

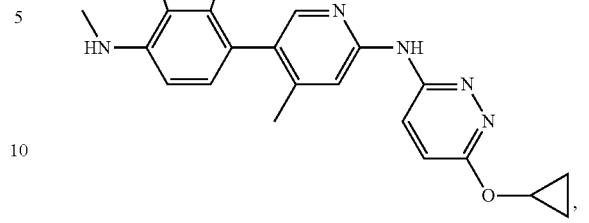

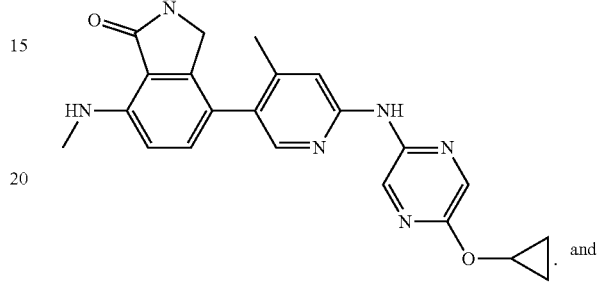

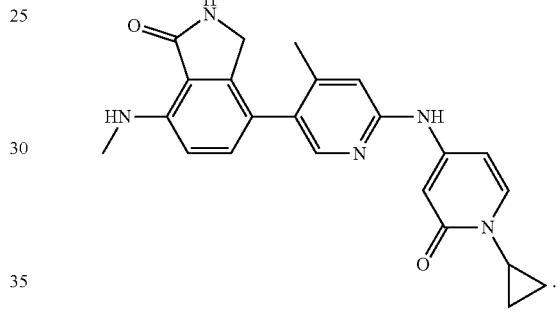

and

18. A pharmaceutical composition, comprising a therapeutically effective amount of the compound, the tautomer or stereoisomer or pharmaceutically acceptable salt thereof according to claim 1 as an active ingredient and a pharmaceutically acceptable carrier.

19. A method for inhibiting colony stimulating factor-1 receptor in a subject in need thereof, comprising administering a therapeutically effective amount of the compound, the tautomer or stereoisomer or the pharmaceutically acceptable salt thereof according to claim 1 to the subject.

* * * * *